United States Patent
Cho

(10) Patent No.: US 10,251,709 B2
(45) Date of Patent: Apr. 9, 2019

(54) ARCHITECTURE, SYSTEM, AND METHOD FOR DEVELOPING AND ROBOTICALLY PERFORMING A MEDICAL PROCEDURE ACTIVITY

(71) Applicant: Samuel Cho, Englewood Cliffs, NJ (US)

(72) Inventor: Samuel Cho, Englewood Cliffs, NJ (US)

(*) Notice: Subject to any disclaimer, the term of this patent is extended or adjusted under 35 U.S.C. 154(b) by 113 days.

(21) Appl. No.: 15/614,535

(22) Filed: Jun. 5, 2017

(65) Prior Publication Data

US 2018/0250075 A1    Sep. 6, 2018

Related U.S. Application Data

(60) Provisional application No. 62/467,240, filed on Mar. 5, 2017.

(51) Int. Cl.

| | | |
|---|---|---|
| *A61B 34/10* | (2016.01) | |
| *A61B 34/35* | (2016.01) | |
| *A61B 34/32* | (2016.01) | |
| *B25J 9/16* | (2006.01) | |
| *A61B 34/20* | (2016.01) | |
| *A61B 34/00* | (2016.01) | |

(52) U.S. Cl.
CPC ............. *A61B 34/10* (2016.02); *A61B 34/20* (2016.02); *A61B 34/32* (2016.02); *A61B 34/35* (2016.02); *B25J 9/1689* (2013.01); *A61B 34/25* (2016.02); *A61B 2034/107* (2016.02); *A61B 2034/108* (2016.02); *A61B 2034/252* (2016.02); *A61B 2034/254* (2016.02); *A61B 2034/258* (2016.02)

(58) Field of Classification Search
CPC ......... A61B 34/10; A61B 34/35; A61B 34/32; A61B 34/20; A61B 2034/108; A61B 2034/254; A61B 2034/107; A61B 2034/258; A61B 2034/252; A61B 34/25; B25J 9/1689
USPC ........................................................ 700/245
See application file for complete search history.

(56) References Cited

U.S. PATENT DOCUMENTS

| | | | | |
|---|---|---|---|---|
| 9,569,589 | B1* | 2/2017 | LaBorde | ................ G16H 50/30 |
| 9,788,907 | B1* | 10/2017 | Alvi | ....................... G16H 15/00 |
| 2004/0024311 | A1* | 2/2004 | Quaid, III | .......... A61B 17/3403 600/428 |
| 2007/0162164 | A1* | 7/2007 | Dariush | ................. B25J 9/1602 700/61 |
| 2011/0015649 | A1* | 1/2011 | Anvari | .................... A61B 34/30 606/130 |
| 2012/0078062 | A1* | 3/2012 | Bagchi | ..................... A61B 5/00 600/300 |
| 2012/0190981 | A1* | 7/2012 | Harris | .................... A61B 34/30 600/439 |
| 2014/0081659 | A1* | 3/2014 | Nawana | ................. G16H 50/20 705/3 |

(Continued)

*Primary Examiner* — Jaime Figueroa
(74) *Attorney, Agent, or Firm* — Merle W. Richman, III

(57) ABSTRACT

Embodiments of architecture, systems, and methods to develop a learning/evolving system to robotically perform one or more activities of a medical procedure where the medical procedure may include diagnosing a patient's medical condition(s), treating medical condition(s), and robotically diagnosing a patient's medical condition(s) and performing one or more medical procedure activities based on the diagnosis without User intervention.

20 Claims, 38 Drawing Sheets

(56) References Cited

U.S. PATENT DOCUMENTS

| | | | |
|---|---|---|---|
| 2014/0276092 A1* | 9/2014 | Tenney | A61B 5/1072 600/476 |
| 2015/0112901 A1* | 4/2015 | Singer | A61B 5/7275 706/12 |
| 2016/0027342 A1* | 1/2016 | Ben-Haim | A61B 5/4035 434/272 |
| 2016/0067007 A1* | 3/2016 | Piron | A61B 5/7246 705/3 |
| 2016/0306943 A1* | 10/2016 | Choi | A61B 5/72 |
| 2016/0314710 A1* | 10/2016 | Jarc | G09B 23/285 |
| 2017/0151025 A1* | 6/2017 | Mewes | A61B 34/10 |
| 2017/0188993 A1* | 7/2017 | Hamilton | A61B 8/4218 |
| 2017/0323064 A1* | 11/2017 | Bates | G06F 19/325 |
| 2017/0360521 A1* | 12/2017 | Johnson | A61B 34/74 |
| 2018/0161098 A1* | 6/2018 | Gupta | A61B 34/10 |
| 2018/0174068 A1* | 6/2018 | Dahl | G06N 99/005 |
| 2018/0177555 A1* | 6/2018 | Cathier | G06F 19/321 |
| 2018/0308569 A1* | 10/2018 | Luellen | G16H 20/10 |

\* cited by examiner

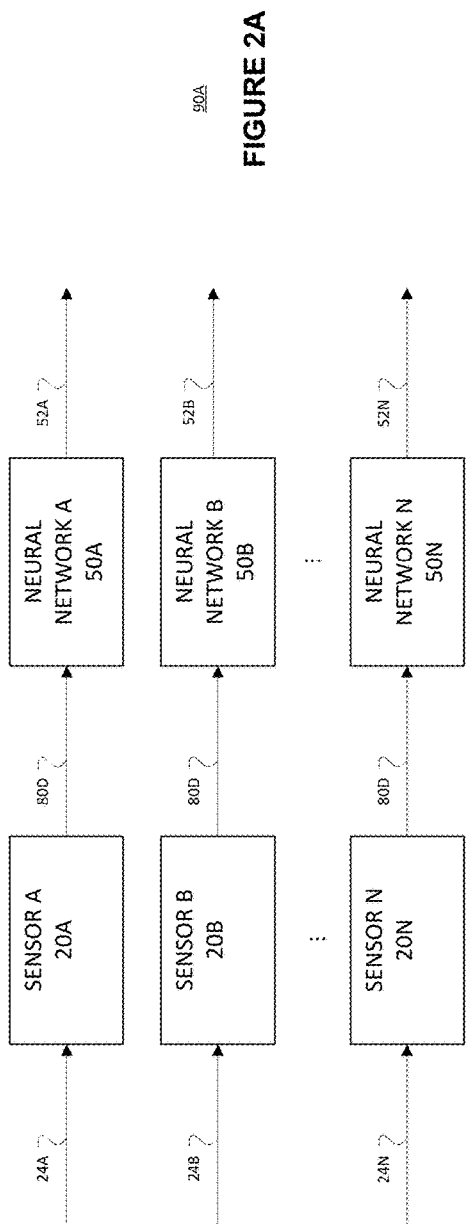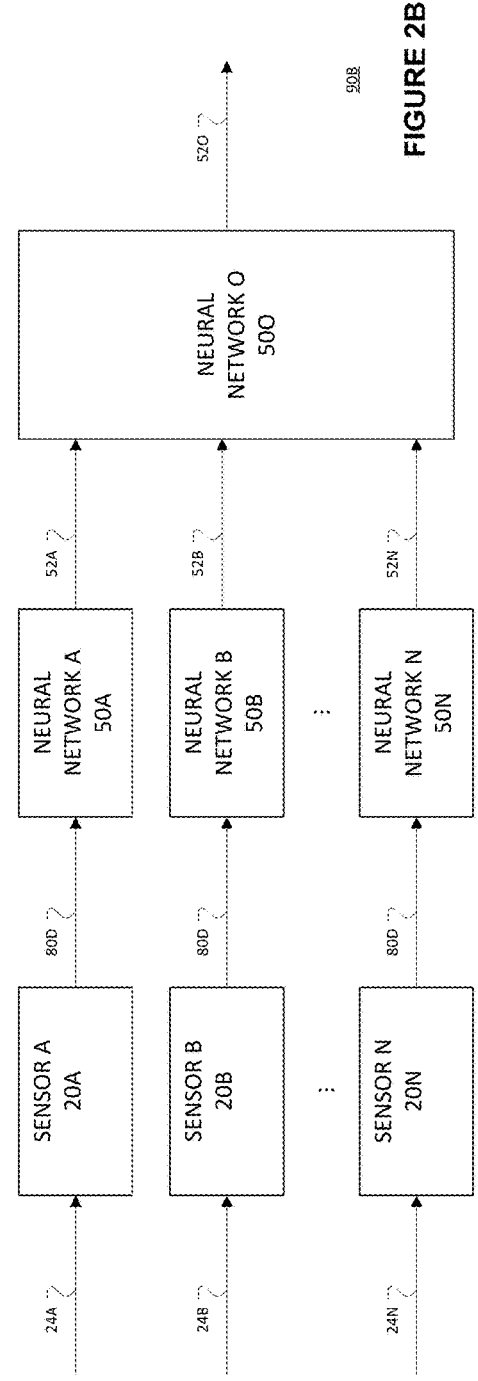

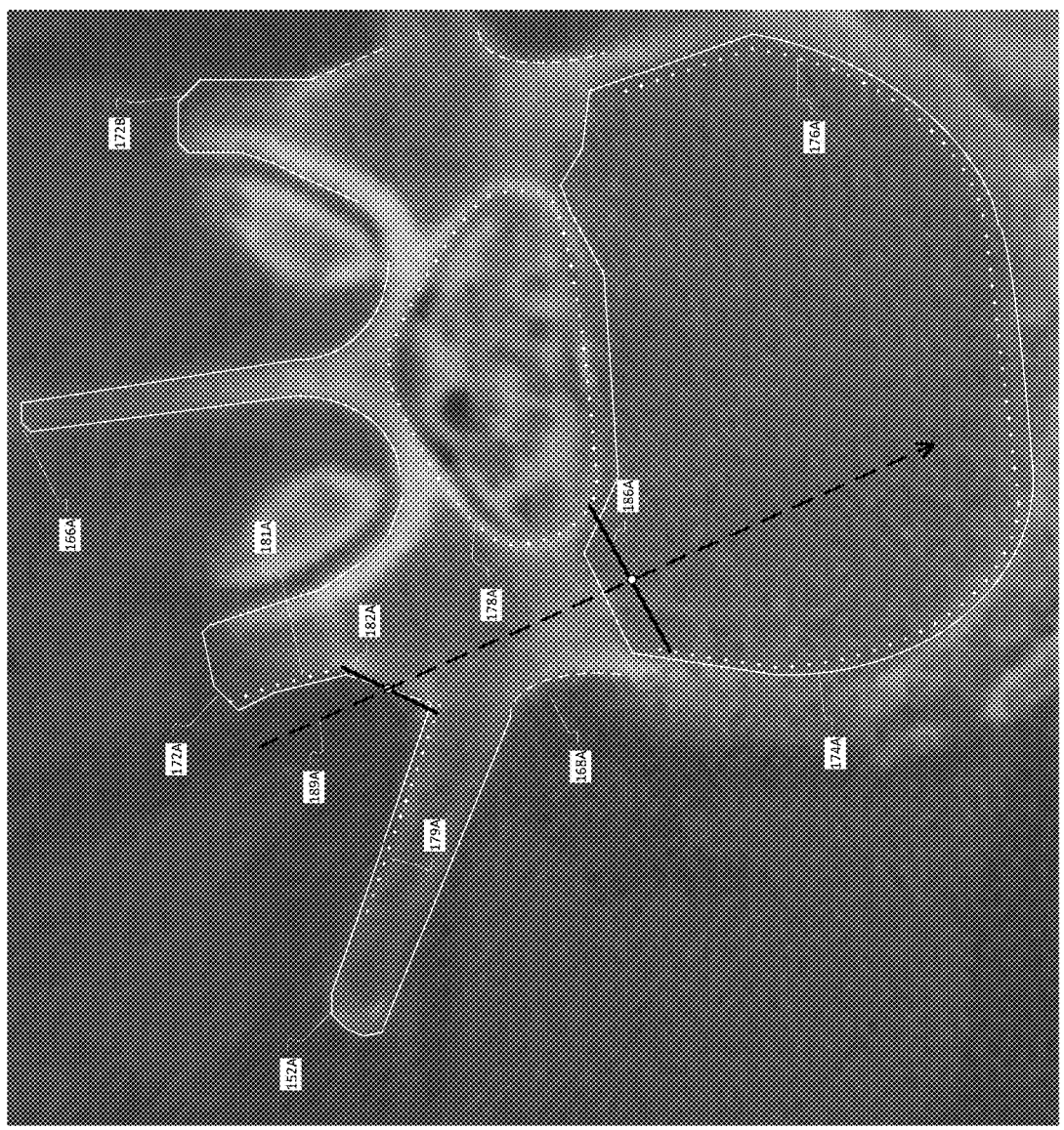

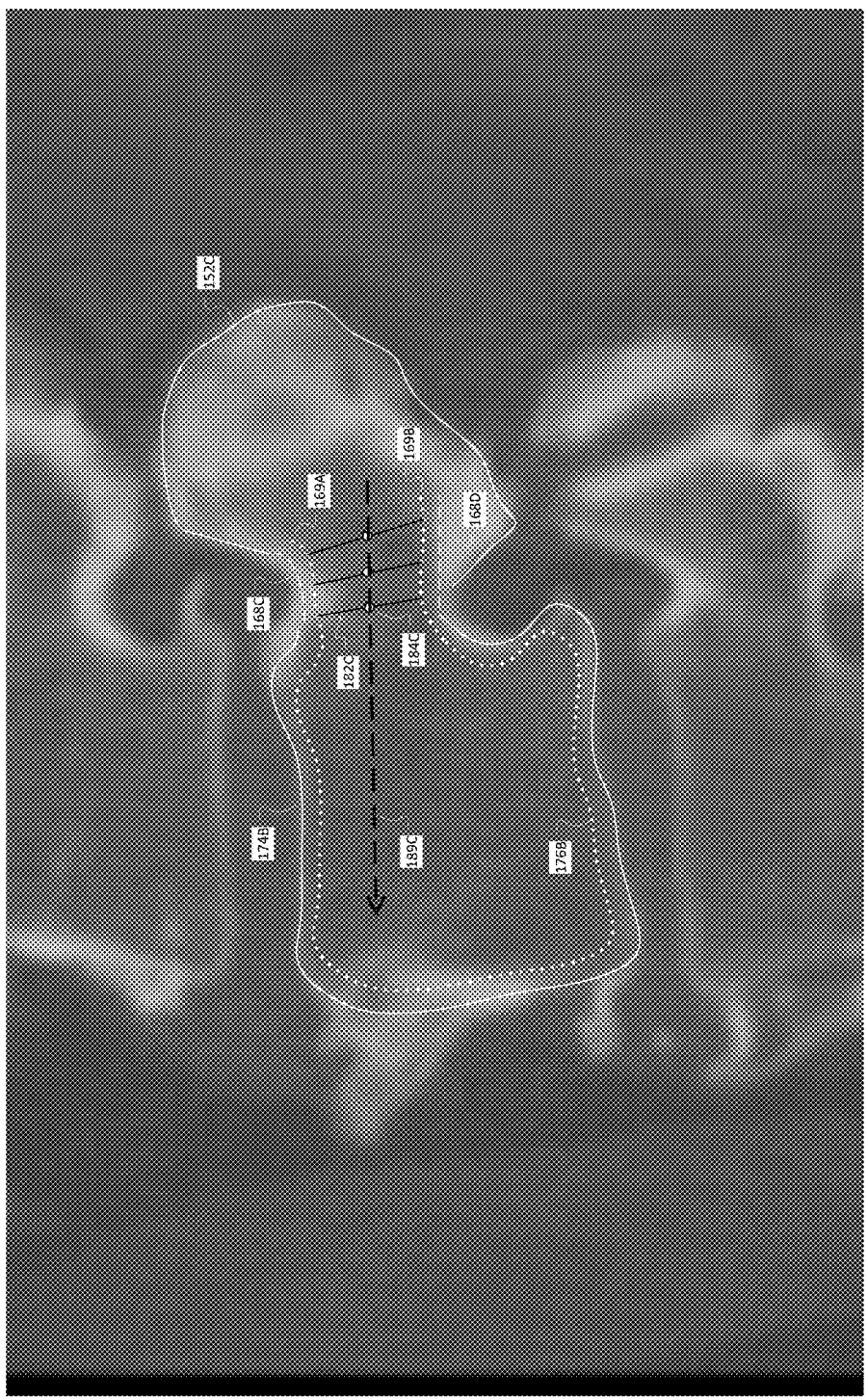

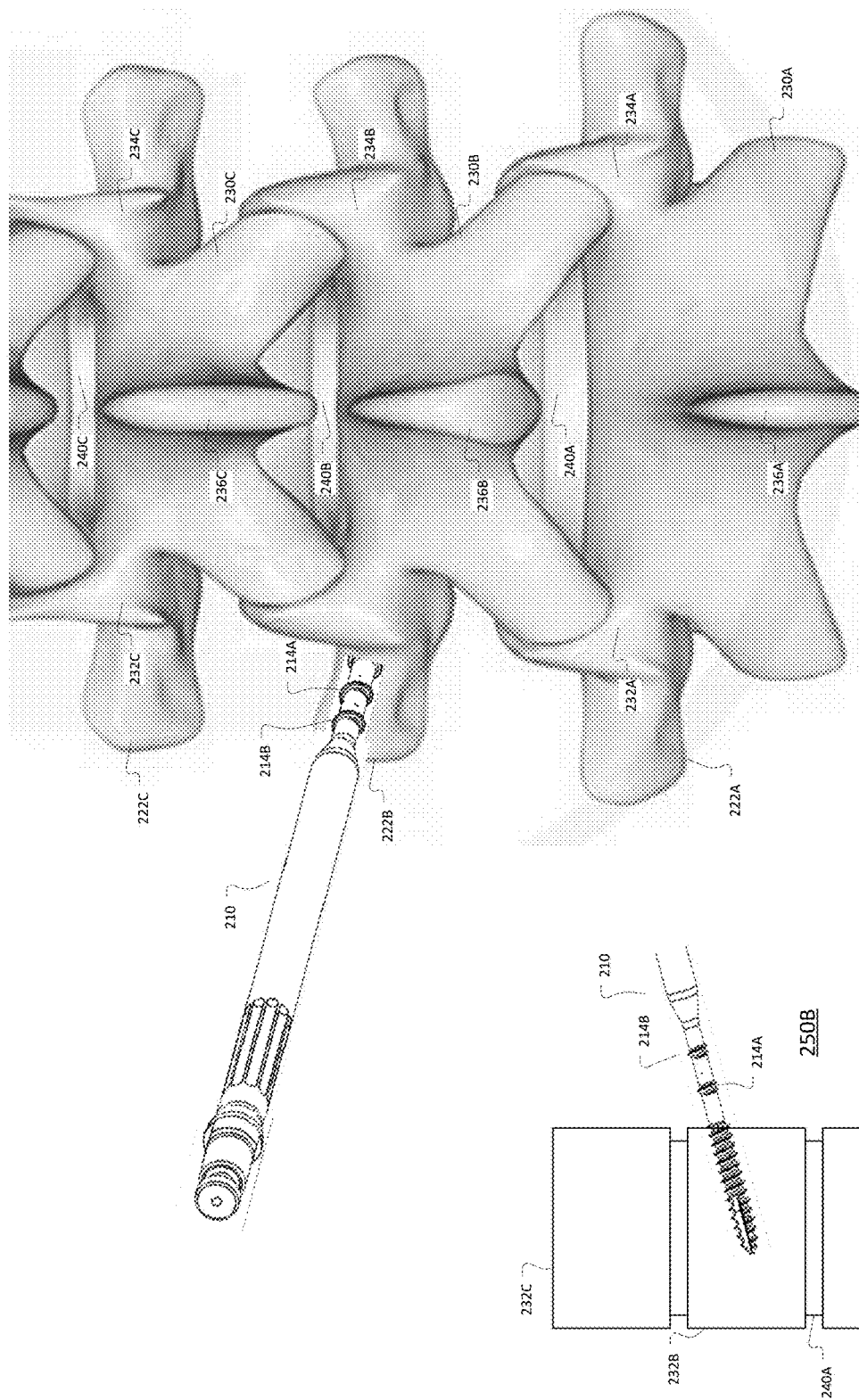

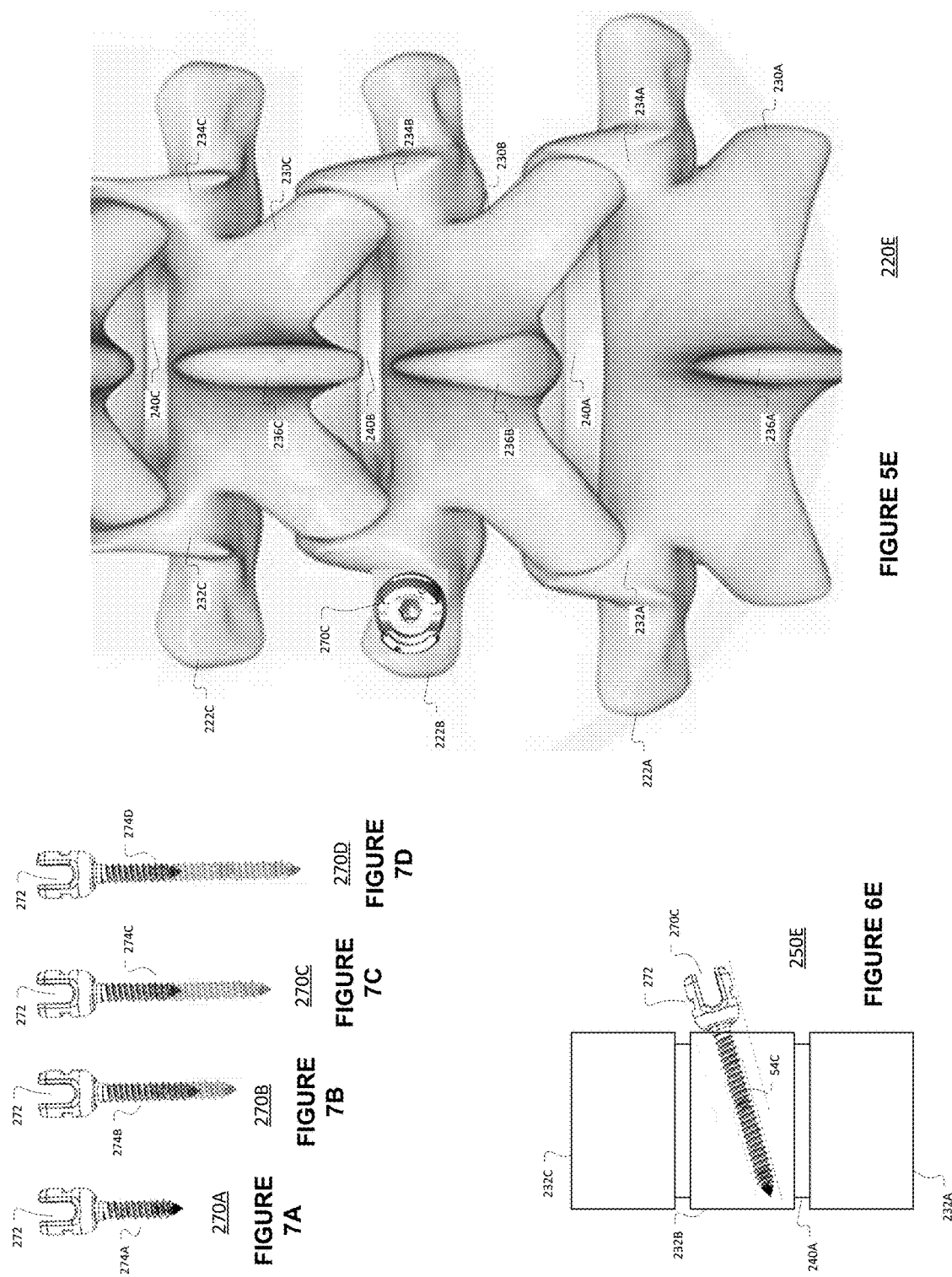

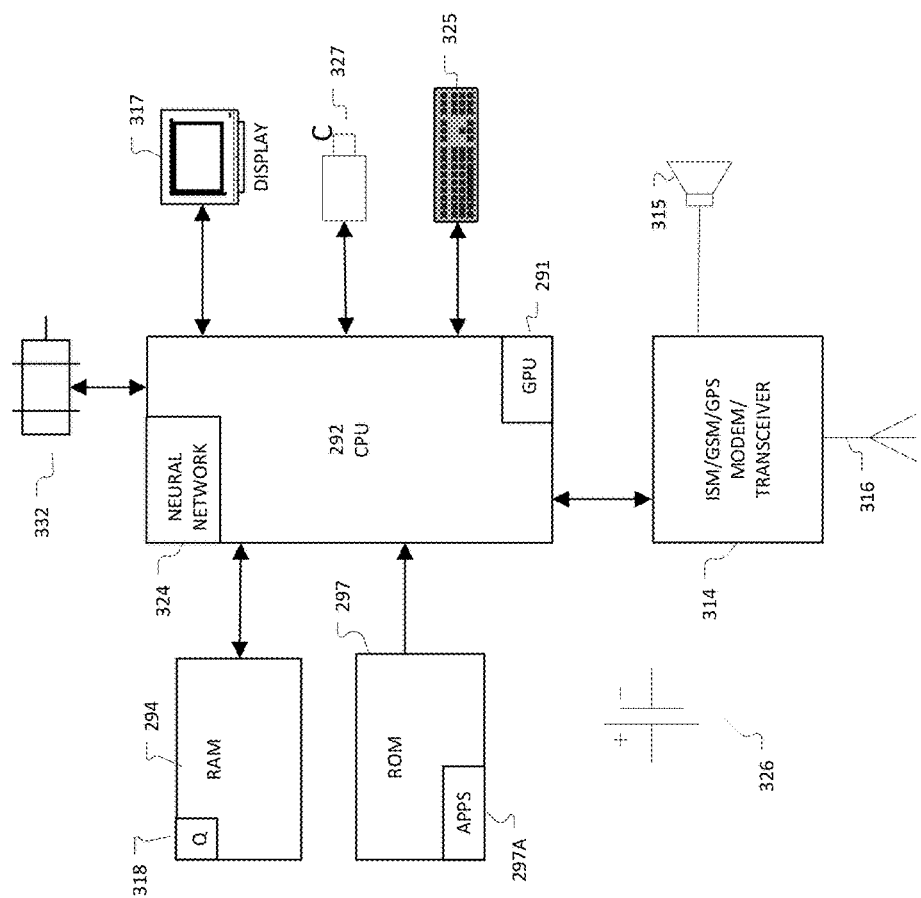

ARCHITECTURE, SYSTEM, AND METHOD FOR DEVELOPING AND ROBOTICALLY PERFORMING A MEDICAL PROCEDURE ACTIVITY

TECHNICAL FIELD

Various embodiments described herein relate to apparatus and methods for developing and robotically performing a medical procedure in part via machine learning.

BACKGROUND INFORMATION

It may be desirable to develop a learning/evolving system to robotically perform one or more activities of a medical procedure where the medical procedure may include diagnosing a patient's medical condition(s), treating medical condition(s), and robotically diagnosing a patient's medical condition(s) and performing one or more medical procedure activities based on the diagnosis without User intervention. The present invention provides architecture, systems, and methods for same.

BRIEF DESCRIPTION OF THE DRAWINGS

FIG. 2A is a diagram of a first sensor system and neural network architecture according to various embodiments.

FIG. 2B is a diagram of a second sensor system and neural network architecture according to various embodiments.

FIGS. 4C to 4O are an axial or cross sectional view of spinal vertebra from a computed tomography scan including segments of a L/M/P being developed to determine target screw trajectories according to various embodiments.

FIGS. 4Q to 4W are sagittal or side view of spinal vertebra from a computed tomography scan including segments of a L/M/P being developed to determine a target screw trajectory according to various embodiments.

FIGS. 5A to 5D are simplified posterior diagrams of a bony segment tap being deployed into a spinal vertebra according to various embodiments.

FIG. 5E is a simplified posterior diagram of a bony segment implant coupled to a spinal vertebra according to various embodiments.

FIGS. 6A to 6D are simplified side or sagittal, sectional diagrams of a bony segment tap being deployed into a spinal vertebra according to various embodiments.

FIG. 6E is a simplified side or sagittal, sectional diagram of a bony segment implant coupled to a spinal vertebra according to various embodiments.

FIG. 7A to 7D are simplified front diagrams of mammalian bony segment threaded implants according to various embodiments.

FIG. 8 is a block diagram of an article according to various embodiments.

DETAILED DESCRIPTION

Figure 1:
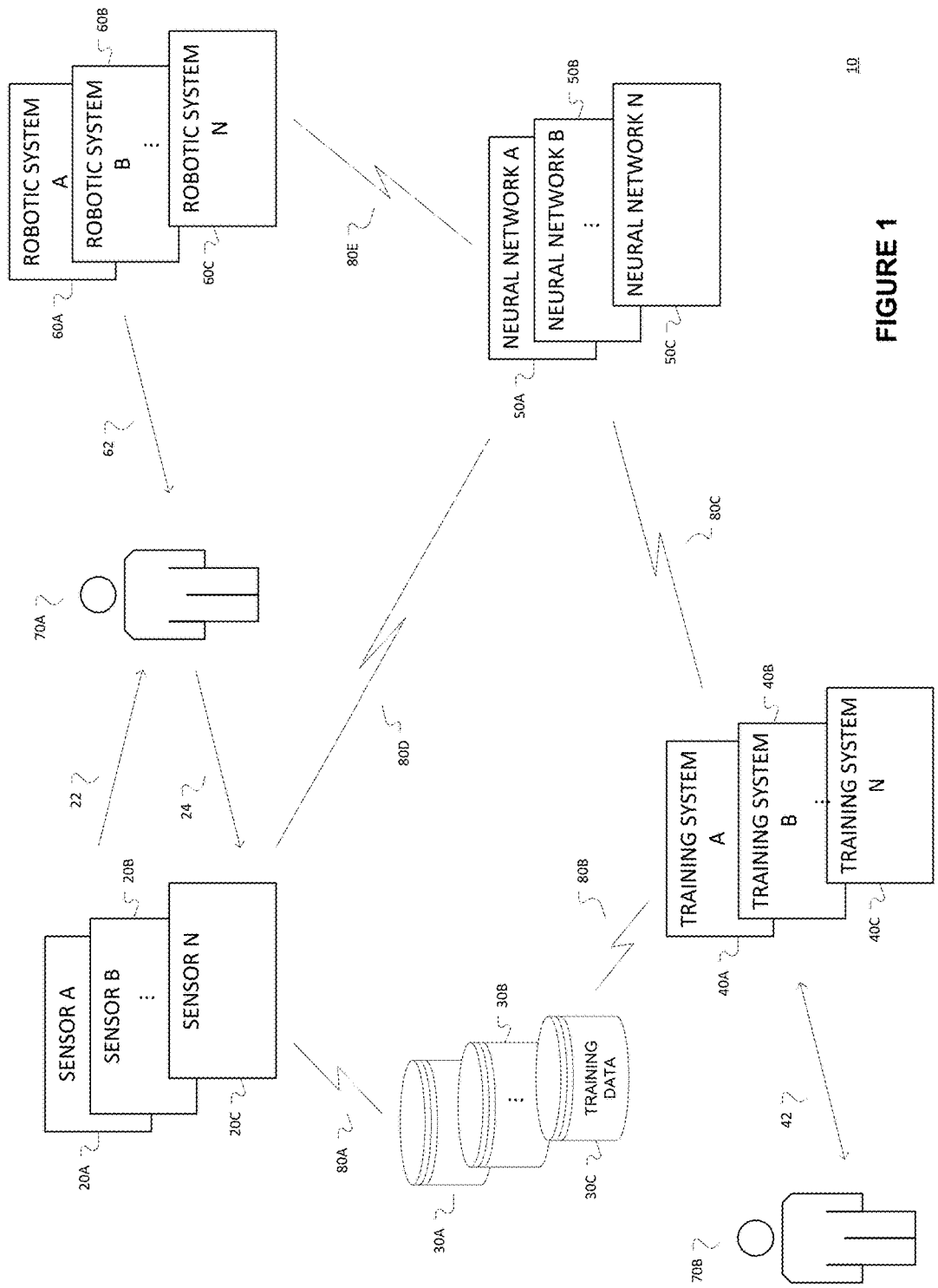
FIG. 1 is a diagram of an architecture for developing a learning/evolving system and robotically/autonomously performing a medical procedure activity according to various embodiments.

The present invention provides an architecture (10—FIG. 1) for developing a base logic/model/procedure (L/M/P) and training/improving neural network systems to enable robot(s) to perform one or more activities of a medical procedure according to various embodiments. Embodiments of the present invention may be employed to continuously train architecture 10 to diagnosis medical condition(s) and treat medical condition(s) where the architecture may evolve or improve based on continuous training. As described below, architecture 10 may be employed to perform one or more activities of a medical procedure that may be employed by medical professionals to diagnosis medical conditions or treat medical conditions. In an embodiment, architecture 10 may divide a medical procedure into a plurality of predefined series of steps or activities to be performed by robotic systems A-N 60A-60C based on feedback or input from sensor systems A-N 20A-20C under control of neural network systems 50A-50C to diagnosis medical conditions or treat medical conditions.

A base logic/model(s)/procedure (L/M/P) may be developed for the step or activities based on available sensor data. Machine learning may be employed to train one or more robots to perform the step or activities based on the developed L/M/P. The robots may then be employed to perform the steps or activities based on the developed L/M/P and live sensor data. The machine learning may be improved or evolved via additional sensor data and User input/guidance.

In an embodiment, a medical professional 70B may be directed to perform various activities of a medical procedure employed on a patient 70A while sensor systems 20A-20C record various data about a patient 70A and medical instruments, implants, and other medical implements employed by a medical professional 70B to perform an activity of a medical procedure. The sensor systems 20A-20C generated, received, and position data may be stored in training databases 30A-30C. Based on the sensor data, system experts/users, and medical professionals 70B inputs a base logic/model(s)/procedure (L/M/P) may be developed for the activities of a medical procedure.

Training systems A-N 40A-40C may use retrieve training data 30A-30C, live sensor system 20A-20C generated, received, and position data, and medical professional(s) 70B input to employ machine learning (form artificial neural network (neural networks) systems A-N 50A-50C in an embodiment) to control operation of one or more robotic systems 60A-60C and sensor system 20A-20C to perform an activity of a medical procedure based on sensor systems A-N 20A-20C live generated, received, and position data based on the developed L/M/P. It is noted that a sensor system A-N 20A-20C may be part of a robotic system A-N 60A-60C and be controlled by a machine learning system (neural network system A-N 50A-50C in an embodiment) including its position relative to a patient and signals it generates (for active sensor systems).

Similarly, a neural network system A-N 50A-50C may also be part of a robotic system A-N 60A-C in an embodiment. In an embodiment, the neural network systems A-N 50A-50C may be any machine learning systems, artificial intelligence systems, or other logic based learning systems, networks, or architecture.

FIG. 1 is a diagram of architecture 10 for developing a learning/evolving system and robotically/autonomously performing a medical procedure activity according to various embodiments. As shown in FIG. 1, architecture 10 may include a plurality of sensor systems A-N 20A-20C, a plurality of training databases 30A-30C, a plurality of training systems A-N 40A-40C, a plurality of neural network systems A-N 50A-50C, and a plurality of robotic systems A-N 60A-60C. Architecture 10 may be directed to a patient 70A and controlled/developed or modulated by one or more system experts and medical professionals 70B. In an embodiment, a sensor system A-N 20A-20C may be a passive or active system. For an active system, a sensor system A-N 20A-20C may generate signal(s) 22 that are configured to activate, highlight, locate, or identify one or more physical attributes of a patient 70A, the patient's 70A environment, medical instrument(s) being deployed to evaluate or treat a patient 70A, and medical constructs being employed on or within a patient 70A. An active sensor system A-N 20A-20C may receive signal(s) 24 that may be generated in part in response to the signal(s) 22 or may be independent of the signal(s) 22. The active sensor system A-N 20A-20C to be deployed/employed/positioned in architecture 10 may vary as a function of the medical procedure activity to be conducted by architecture 10 and may include electro-magnetic sensor systems, electrical stimulation systems, chemically based sensors, and optical sensor systems.

In a passive system, a sensor system A-N 20A-20C may receive signal(s) 24 that may be generated in response to other stimuli including electro-magnetic, optical, chemical, temperature, or other patient 70A measurable stimuli. A passive sensor system A-N 20A-20C to be deployed/employed/positioned in architecture 10 may also vary as a function of the medical procedure activity to be conducted by architecture 10 and may include electro-magnetic sensor systems, electrical systems, chemically based sensors, and optical sensor systems.

Sensor system A-N 20A-20C signals (generated and received/measured, position relative to patient) 22, 24 may be stored in training databases 30A-30C during training events and non-training medical procedure activities. In an embodiment, architecture 10 may store sensor system A-N 20A-20C signals 22, 24 (generated, received, and position data) during training and non-training medical procedure activities where the generated, received, and position data may be used by training systems A-N 40A-40C to form and update neural network systems A-N 50A-50C based on developed L/M/P. One or more training system A-N 40A-40C may use data 80B stored in training databases and medical professional(s) 70B feedback or review 42 to generate training signals 80C for use by neural network systems A-N 50A-50C to form or update neural network or networks based on developed L/M/P. The data 80B may be used to initially form the L/M/P for a particular activity of a medical procedure.

The training system data 80C may represent sensor data 80A that was previously recorded for a particular activity of a medical procedure. In an embodiment, when medical professional(s) 70B may perform an activity of a medical procedure, the sensor systems A-N 20A-C may operate to certain attributes as directed by the professional(s) 70B or training systems A-B 40A-C. One or more neural network systems A-N 50A-50C may include neural networks that may be trained to recognize certain sensor signals including multiple sensor inputs from different sensor systems A-N 20A-20C representing different signal types based on the developed L/M/P. The neural network systems A-N 50A-C may use the formed developed L/M/P and live sensor system A-N 20A-20C data 80D to control the operation of one or more robotic systems A-N 60A-60C and sensor systems A-N 20A-20C where the robotic systems A-N 60A-60C and sensor systems A-N 20A-20C may perform steps of a medical procedure activity learned by the neural network systems A-N 50A-C based on the developed L/M/P.

As noted one or more sensor systems A-N 20A-C may be part of a robotic system A-N 60A-60C or a neural network system A-N 50A-50C. A sensor system A-N 20A-C may also be an independent system. In either configuration sensor system's A-N 20A-C generated signals (for active sensors) and position(s) relative to a patient during an activity may be controlled by a neural network system A-N 50A-50C based on the developed L/M/P. Similarly, one or more training systems A-N 20A-C may be part of a robotic system A-N 60A-60C or a neural network system A-N 50A-50C. A training system A-N 40A-C may also be an independent system. In addition, a training system A-N 40A-C may also be able to communicate with a neural network system A-N 50A-50C via a wired or wireless network. In addition, one or more training databases 30A-C may be part of a training system A-N 40A-40C. A training database 30A-C may also be an independent system and communicate with a training system A-N 40A-40C or sensor system A-N 20A-C via a wired or wireless network. In an embodiment, the wired or wireless network may be local, network or network (Internet) and employ cellular, WiFi, and satellite communication systems.

FIG. 2A is a diagram of a first sensor system and neural network architecture 90A according to various embodiments. As shown in FIG. 2A, each sensor system A-N 20A-20C may be coupled to a separate neural network system 50A-N. In such an embodiment, a neural network system A-N 50A-C may be trained to respond to particular sensor data (generated, received, and position) based on one or more developed L/M/P. The neural network system A-N 50A-C outputs 52A-N may be used individually to control a robotic system A-N 60A-C. In another embodiment, the neural network systems A-N 50A-50C may be coupled to another neural network system O 50O as shown in FIG. 2B. The neural network architecture 90B may enable neural network systems A-N 50A-N to process data from sensor systems A-N 20A-20C and neural network system O 50O to process the neural network systems A-N 50A-O outputs 52A-52N. The neural network system O 50O may then control one or more robotic systems A-N 60A-C and sensor systems A-N 20A-20C based on neural processing of combined neural processed sensor data. The neural network system O 50O may be able to make decisions based on a combination of different sensor data from different sensor systems A-N 20A-20C and based on one or more developed L/M/P, making the neural network system O 50O more closely model a medical professional 70B, which may consider many different sensor data types in addition to their sensory inputs when formulating an action or decision.

Figure 2C:
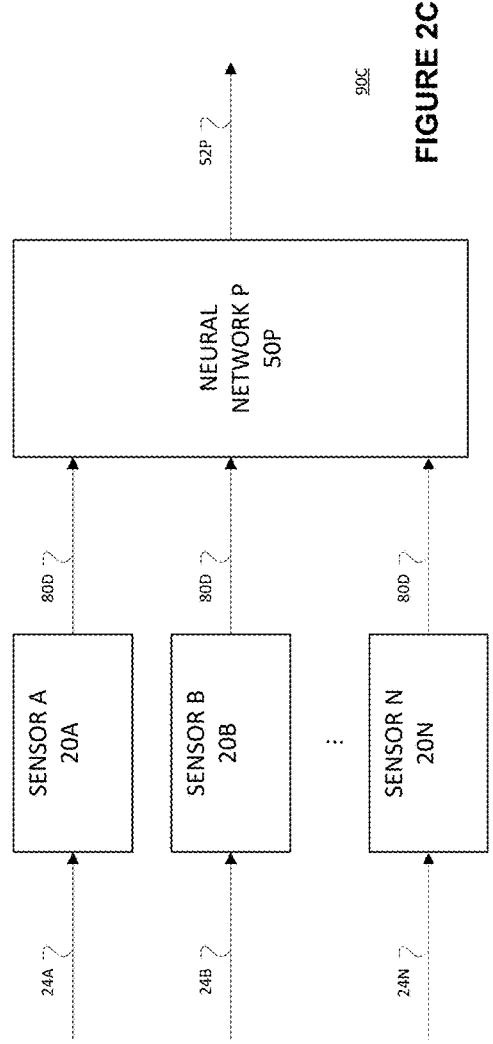
FIG. 2C is a diagram of a third sensor system and neural network architecture according to various embodiments.
Figure 2D:
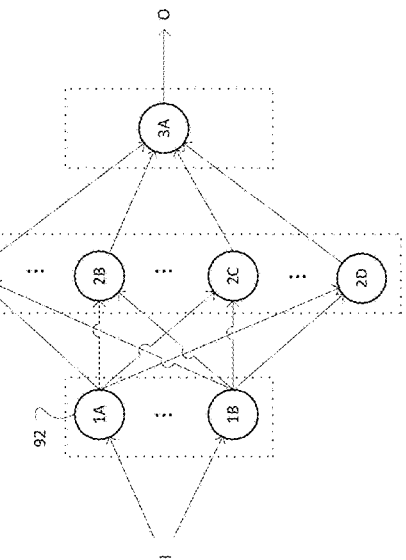
FIG. 2D is a diagram of a data processing module network according to various embodiments.

In a further embodiment, a neural network architecture 90C shown in FIG. 2C may employ a single neural network system P 50P receiving and processing sensor data 80D from a plurality of sensor systems A-N 20A-20C. Similar to the neural network system O 50O, the single neural network system P 50P may be able to make decisions based on a combination of different sensor data from different sensor systems A-N 20A-20C, making the single neural network system P 50P also more closely model a medical professional 70B, which may consider many different sensor data types in addition to their sensory inputs when formulating an action or decision. In an embodiment any of the neural architectures 90A-C may employ millions of nodes configured in various configurations including a feed forward network as shown in FIG. 2D where each column of nodes 1A-1B, 2A-D, 3A, feeds the next right column of nodes. The input vector I and output vector O may include many entries and each node may include a weighted matrix that is applied to the upstream vector where the weight matrix is developed by the training database 30A-30C and training systems A-N 40A-40C.

Different sets of neural networks 90A-90D may be trained/formed and updated (evolve) for a particular activity of a medical procedure. One or more L/M/P may be developed based on availability of sensor data 80A to perform a particular activity of a medical procedure. The different sets of neural networks 90A-90D may be trained/formed and updated (evolve) for a particular activity of a medical procedure based on the developed one or more L/M/P.

Figure 3A:
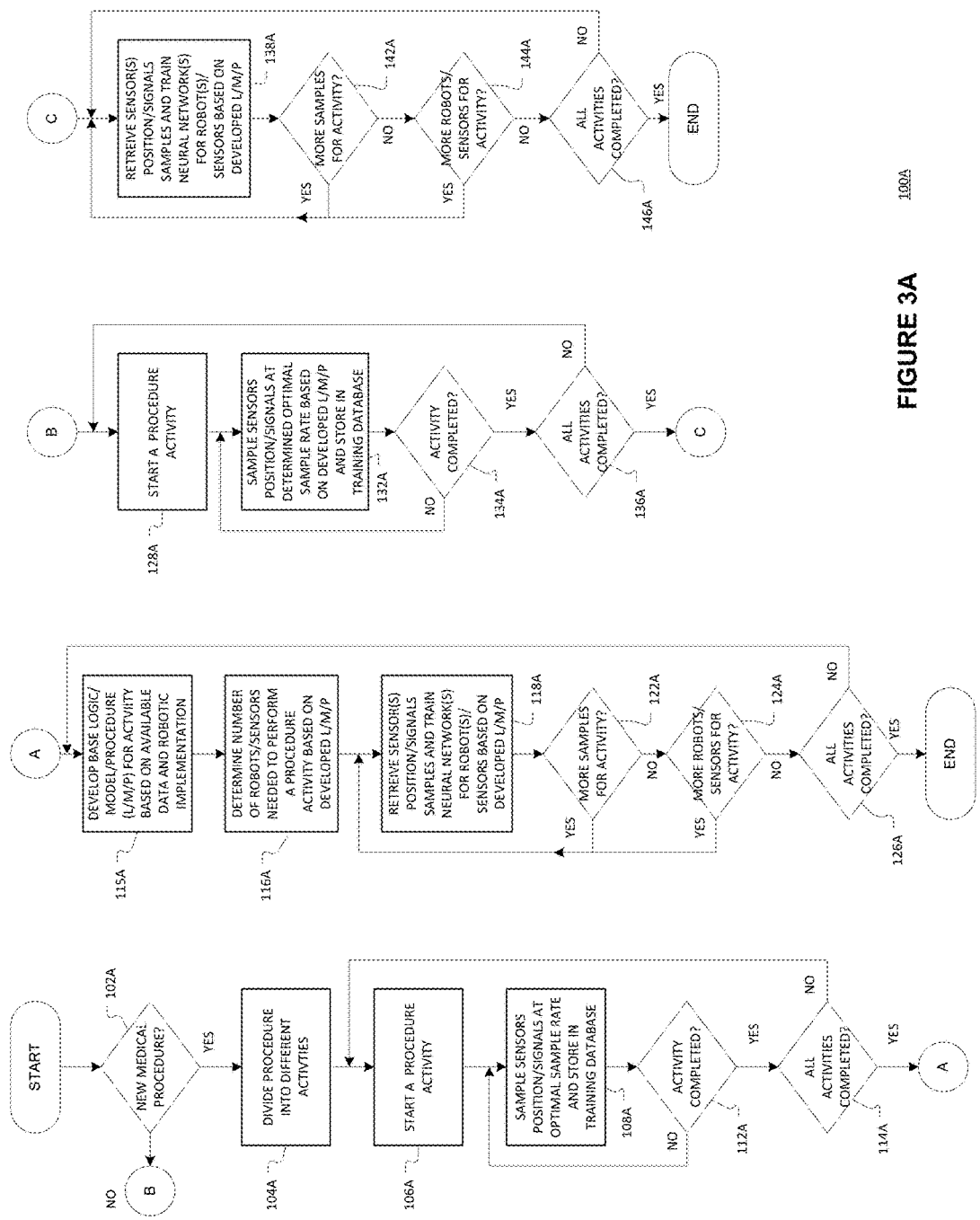
FIG. 3A is a flow diagram illustrating several methods for developing a base logic/model/procedure (L/M/P) and training/improving neural network systems to enable robot(s) to perform activities of a medical procedure based on a developed L/M/P according to various embodiments.

FIG. 3A is a flow diagram illustrating several methods 100A for developing one or more base logic/model/procedure (L/M/P) and training/improving neural network systems 50A-50C to enable robot(s) 60A-60C to perform activities of a medical procedure based on a developed L/M/P and sensor systems A-N 20A-20C according to various embodiments. As noted, architecture 10 may be employed to develop/evolve one or more L/M/P and train neural network systems 50A-N to operate one or more robotic systems 60A-N and sensor systems A-N 20A-20C based on one or more developed L/M/P and sensor data (generated, received, and position) 80A for one or more sensor systems 20A-20C and employed by one or more training systems 40A-40C where the sensor data 80A may be stored in one or more training databases 30A-30C.

As shown in FIG. 3A and discussed above architecture 10 may be employed to develop one or more logic/models/procedures (L/M/P) for a new activity of a medical procedure or continue to update/evolve one or more logic/models/procedures (L/M/P) of a previously analyzed activity of a medical procedure. In addition, architecture 10 may be used to train one or more neural network systems 50A-50C (or other automated systems) for a new activity of a medical procedure or continue to update or improve neural network systems 50A-50C training for a previously analyzed activity of a medical procedure based on the developed one or more L/M/P and available sensor data 80A.

As shown in FIG. 3A, a training system 40A-40C, expert, or medical professional 70B may determine whether a medical procedure selected for review by architecture 10 has been reviewed/analyzed previously (activity 102A). If the medical procedure has been reviewed/analyzed previously, new data may be collected for one of the known activities of the medical procedures (activities 128A-134A) to improve evolve one or more developed L/M/P and related machine learning systems (neural networks 50A-C in an embodiment). Otherwise, a medical professional or other user/expert 70B or training system(s) 40A-40C may divide the medical procedure into discrete, different activities (activity 104A).

A medical professional or other user 70B may be able to indicate the one or more activities that underlie a medical procedure. Depending on the medical procedure there may be activities defined by various medical groups or boards (such the American Board of Orthopaedic Surgery "ABOS") where a medical professional 70B certified in the procedure is expected to perform each activity as defined by a medical group or boards. In an embodiment, a medical professional 70B may also define a new medical procedure and its underlying activities. For example, a medical procedure for performing spinal fusion between two adjacent vertebrae may include activities as defined by the ABOS (activity 104A). The medical procedure may be further sub-divided based on the different L/M/P that may be developed/created for each activity.

A simplified medical procedure may include a plurality of activities including placing a pedicle screw in the superior vertebra left pedicle (using sensor system(s) A-N 20A-C to verify its placement), placing a pedicle screw in the inferior vertebra left pedicle (using sensor system(s) A-N 20A-C to verify its placement), placing a pedicle screw in the superior vertebra right pedicle (using sensor system(s) A-N 20A-C to verify its placement), placing a pedicle screw in the inferior vertebra right pedicle (using sensor system(s) A-N 20A-C to verify its placement), loosely coupling a rod between the superior and inferior left pedicle screws, loosely coupling a rod between the superior and inferior right pedicle screws, compressing or distracting the space between the superior and inferior vertebrae, fixably coupling the rod between the superior and inferior left pedicle screws, and fixably coupling the rod between the superior and inferior right pedicle screws.

It is noted that architecture 10 may not be requested or required to perform all the activities of a medical procedure. Certain activities may be performed by a medical professional 70B. For example, architecture 10 may be employed to develop one or more L/M/P and train one or more neural network systems 50A-50C with robotic systems 60A-60C and sensor system(s) A-N 20A-C to insert pedicle screws in left and right pedicles of vertebrae to be coupled based on the developed one or more L/M/P. A medical professional may place rods, compress or decompress vertebrae and lock the rods to the screws. It is further noted that the activities may include multiple steps in an embodiment. Once developed and trained, architecture 10 may be employed to place one or more pedicle screws in vertebrae pedicles.

Figure 4B:
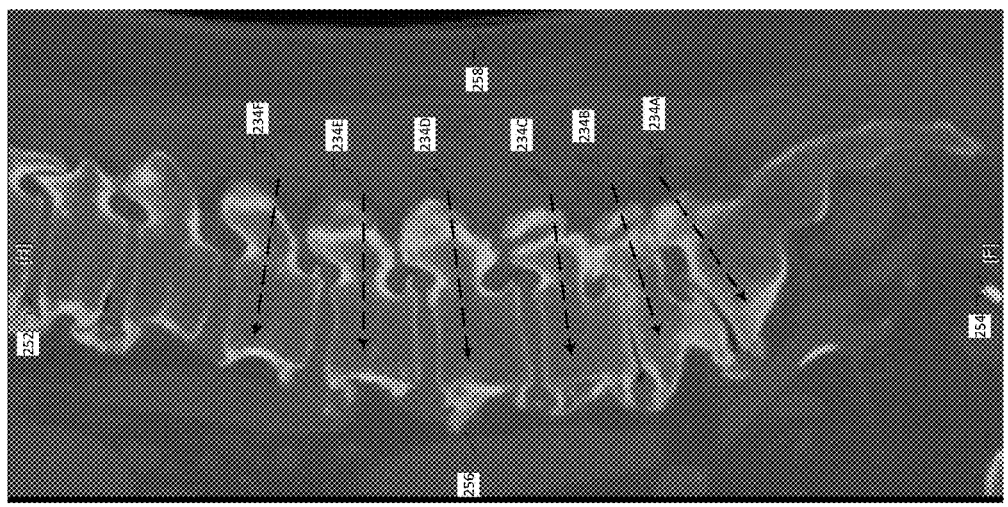
FIG. 4B is a sagittal or side view of spinal vertebra from a computed tomography scan that may be employed by a system to form a L/M/P according to various embodiments.
Figure 4A:
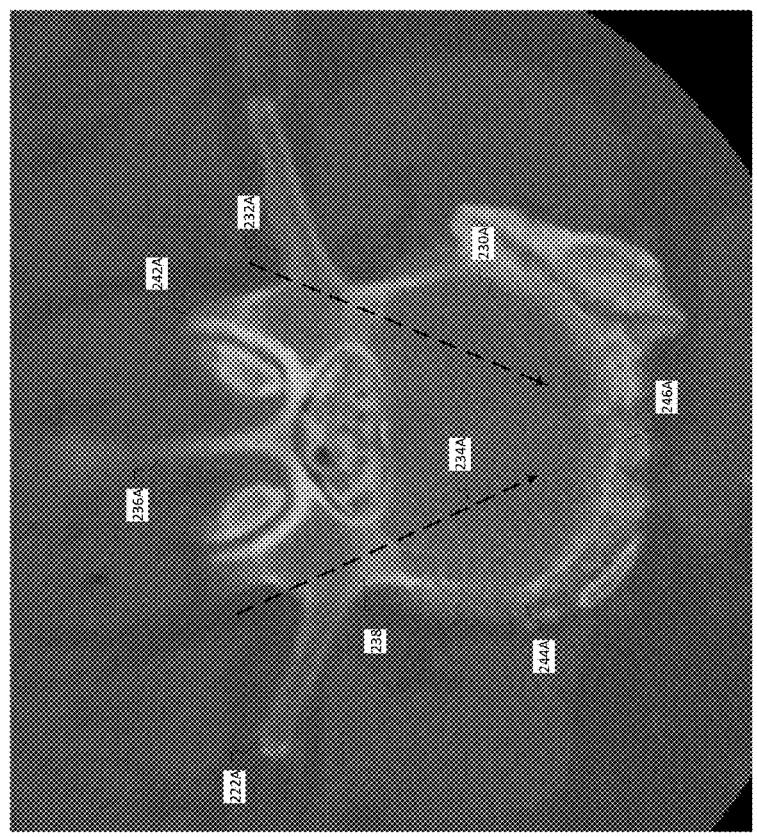
FIG. 4A is an axial or cross sectional view of spinal vertebra from a computed tomography scan that may be employed by a system to form a L/M/P according to various embodiments.

A medical professional 70B or other user may start an activity of a medical procedure (activity 106A), and one or more sensor systems 20A-20C may be employed/positioned to generate (active) and collect sensor data while the activity is performed (activity 108A). Architecture 10 may sample sensor data (generated, received, and position) 80A of one or more sensor systems 20A-20C at an optimal rate to ensure sufficient data is obtained during an activity (activity 108A). For example, the sensor data may include the positions of a radiographic system, its generated signals, and its radiographic images such as images 220A, 220B shown in FIGS. 4A and 4B generated from received data. FIG. 4A is an axial or cross sectional view of a spinal vertebra from a computed tomography scan 230A created by a first sensor system 40A generating a first signal and having a first position relative to a patient according to various embodiments. FIG. 4B is a sagittal or side view of several spinal vertebrae from a computed tomography scan 230A created by a first sensor system 40A generating a second signal and having a s position relative to a patient according to various embodiments.

As shown in FIG. 4A, a vertebrae 230A may include transverse processes 222A, spinous process 236A, pedicle isthmus 238A, facet joint 242A, vertebral cortex 246A, and vertebral body 244A where the pedicle 232A is formed between the transverse processes 222A and facet joint 242A. As part of the training process, a medical professional 70B may insert pedicle screw desired trajectory lines 234A. One or more training systems 40A-40C may enable a medical professional 70B to place pedicle screw desired trajectory line 234A in the radiographic image 220A. The one or more training systems 40A-40C may also enable a medical professional 70B to place pedicle screw desired trajectory lines 234A-234F in the radiographic image 220B.

In detail, architecture 10 may be employed to monitor all the steps a medical professional 70B completes to conduct an activity of a medical procedure to develop one or more base L/M/P (activity 115A) and train one or more neural network networks 50A-50C to control one or more robotic systems 60A-60C and sensor systems 20A-20C to perform the same steps to conduct an activity of a medical procedure based on the one or more L/M/P. For example, for the activity of placing a pedicle screw 270C in the left pedicle 232 of a vertebra 230B (as shown completed in FIGS. 5E and 6E), a medical professional may employ a tap 210 over a guide wire 260 into a pedicle 232 along a desired pedicle screw trajectory (234A FIGS. 4A and 4B). In an embodiment, a medical professional 70B may employ a tap 210 into a pedicle 232 along a desired pedicle screw trajectory 234A without a guide wire 260. In a further embodiment, a medical professional 70B may place a pedicle screw 270C into a pedicle 232 along a desired pedicle screw trajectory without a guide wire 260 or tap 210.

In this activity one or more target trajectory lines 234A, 234D may be needed to accurately place a pedicle screw in a safe and desired location. In an embodiment, the activity may include placing a screw in the right pedicle of the L3 vertebra 256 shown in FIG. 4B. Using available sensor data 80A such as the images shown in FIGS. 4A and 4B, one or more based L/M/P (220E, 220G FIG. 4X) may be developed/used that identifies critical landmarks/shapes in the image and a method of safely, accurately, and repeatably generating screw target trajectories 234A (189A, 189B, 189C in FIG. 4X) from different orientations (axial and sagittal). The L/M/P (220E. 220G FIG. 4X) may be employed by architecture 10 to train neural networks 50A-C and robotically place a screw 270A-D in a right pedicle 232B of a vertebrae 256.

Figure 3B:
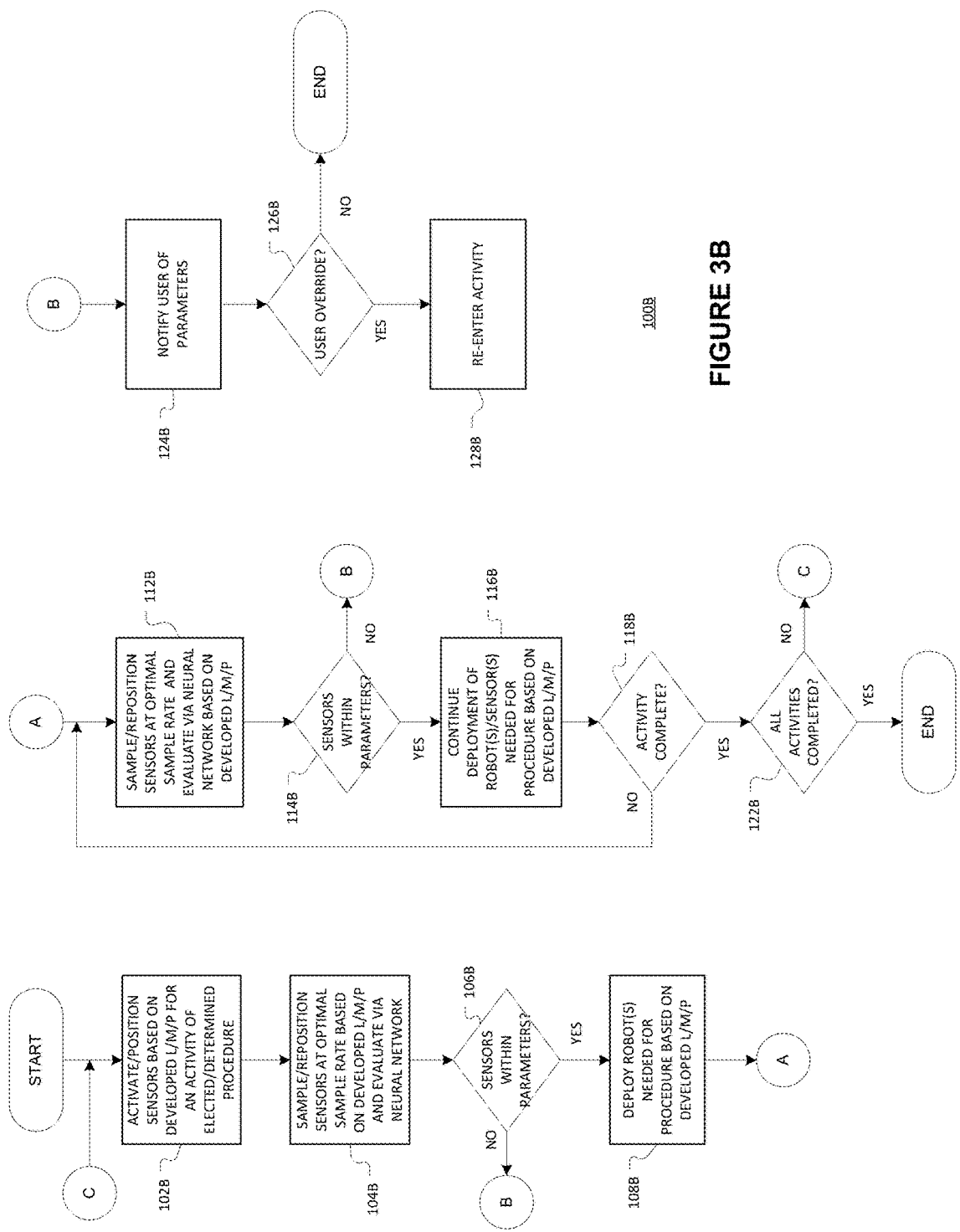
FIG. 3B is a flow diagram illustrating several methods for employing neural network systems to control robot(s) to perform activities of a medical procedure based on a developed L/M/P according to various embodiments.
Figure 3C:
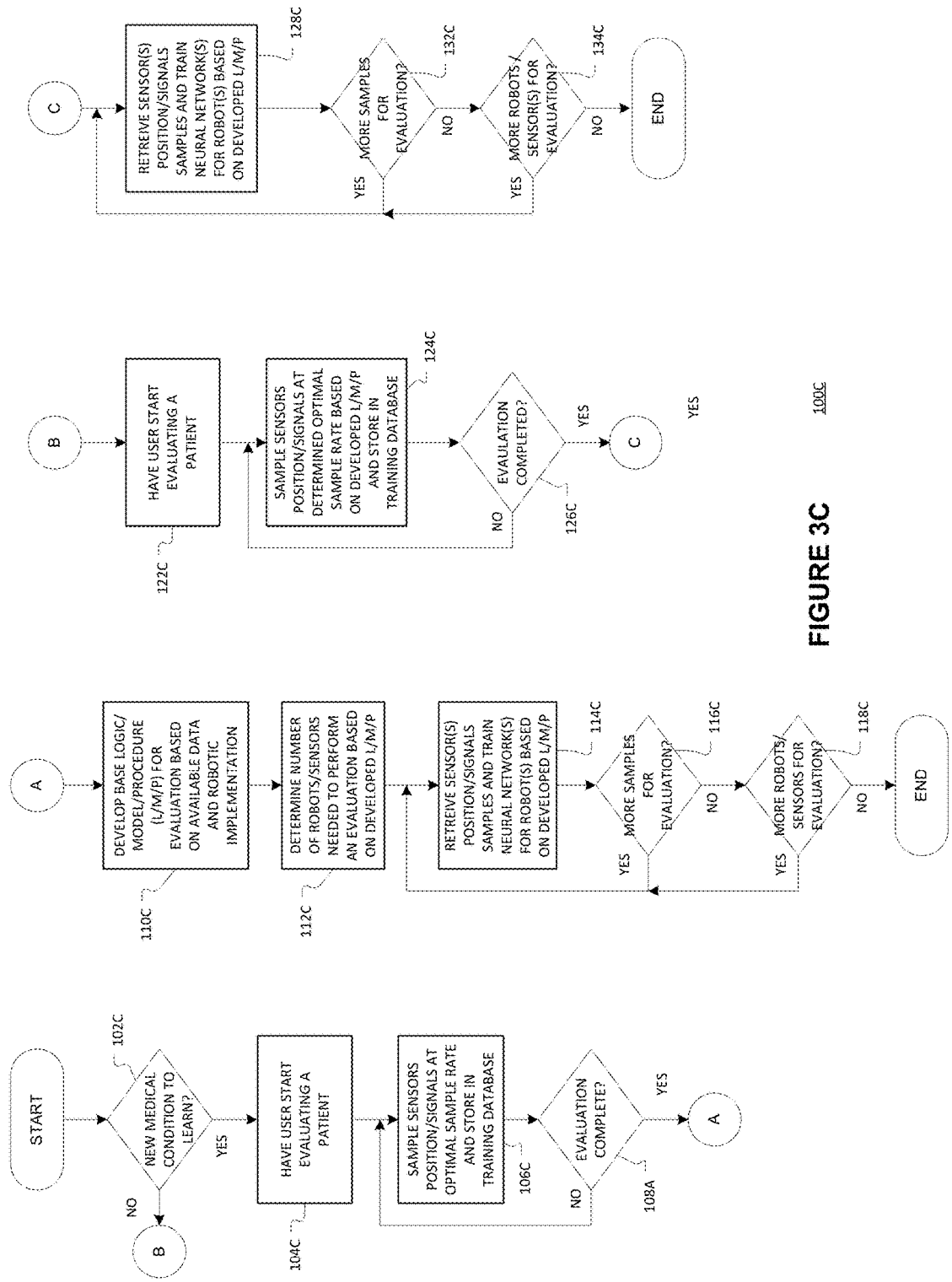
FIG. 3C is a flow diagram illustrating several methods for developing a base logic/model/procedure (L/M/P) and training/improving neural network systems to enable robot(s) to diagnose a medical condition based on a developed L/M/P according to various embodiments.
Figure 3D:
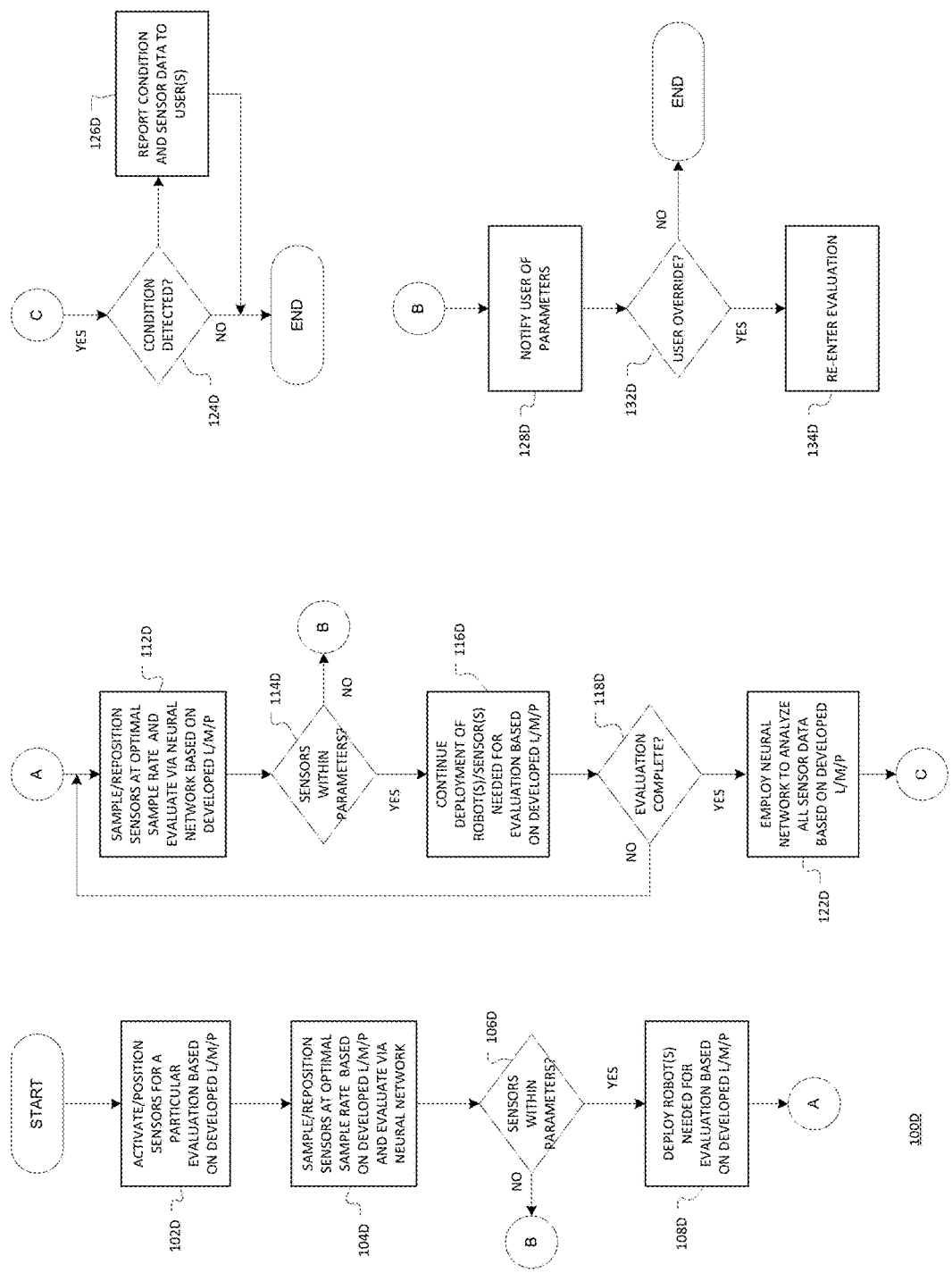
FIG. 3D is a flow diagram illustrating several methods for employing neural network systems to control robot(s) to diagnose a medical condition based on a developed L/M/P according to various embodiments.
Figure 3E:
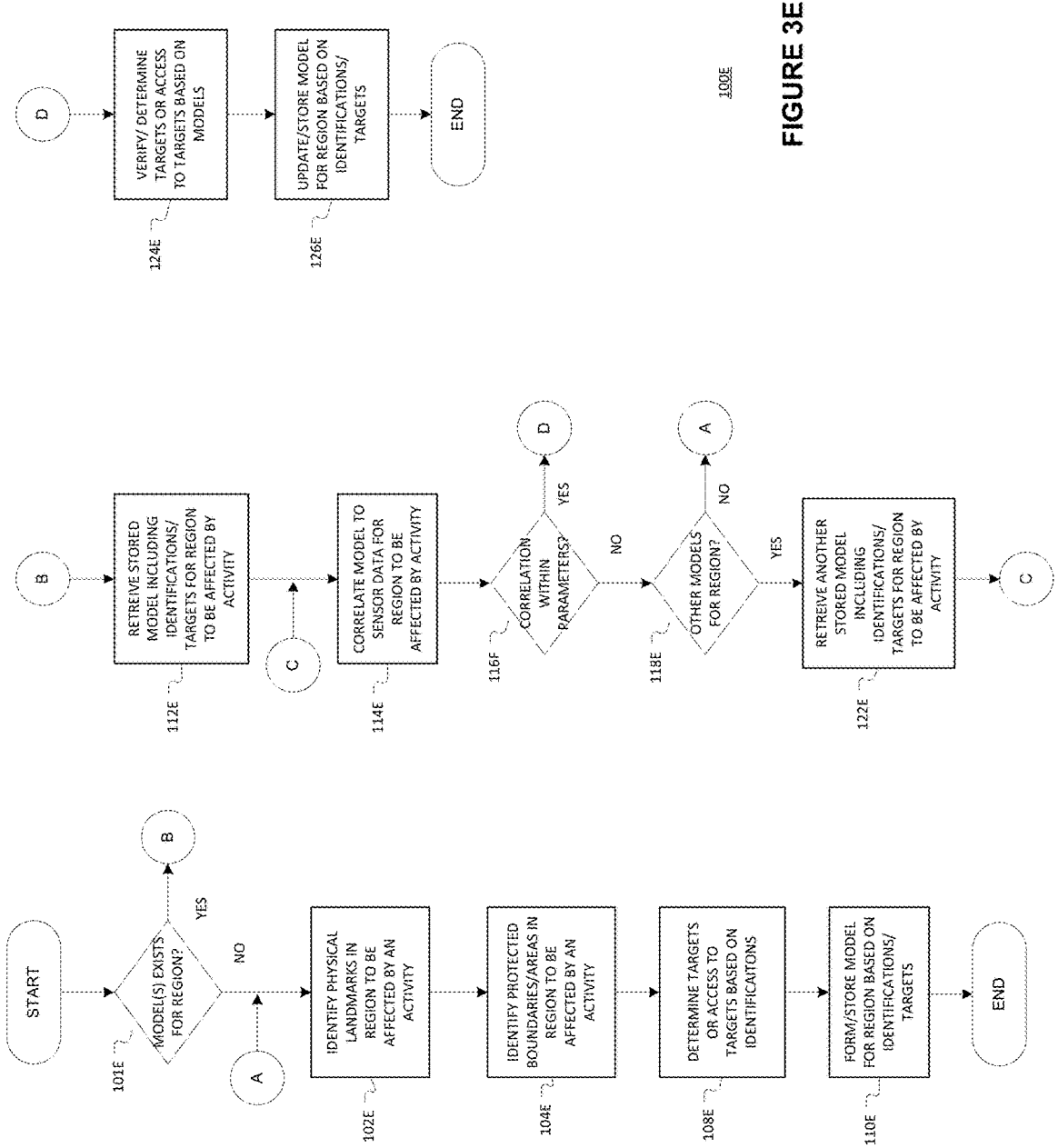
FIG. 3E is a flow diagram illustrating several methods for creating/using a based logic/model/procedure (L/M/P) for a region to be affected by an activity according to various embodiments.

FIG. 3E is a flow diagram illustrating several methods 100E for creating/using a based logic/model/procedure (L/M/P) for a region to be affected by an activity according to various embodiments. In the method 100E, architecture 10 via training systems 30A-30C or neural networks 50A-C may determine whether one or more L/M/P (e.g. 220E, 220G) exists for a particular region to be affected by an activity (activity 101E). In an embodiment, the region may be very specific, e.g., the L3 vertebra 256 right pedicle 232B. There may be one or more different L/M/P developed for each left and right pedicle 232A, 232B of every vertebrae (sacrum, lumbar, thoracic, and cervical) of a human spine. The models may include one or more 2-D orthogonal images enabling an effective 3-D representation of the region or a formed 3-D image in an embodiment.

If one or more L/M/P do not exist for the region to be affected by an activity, a User 70B via architecture 10 or architecture 10 via training systems 40A-40C or neural systems 50A-50C may develop or form and store one or more L/M/P for the region (activities 102E-110E). In an embodiment, physical landmarks or anatomical features in a region to be affected may be identified (activity 102E) and protected areas/anatomical boundaries may also be identified (activity 104E). Based on the identified landmarks and boundaries, targets or access to targets may be determined or calculated in an embodiment (activity 108E). The resultant one or more L/M/P (models in an embodiment) may then be formed (such a 3-D model from two or more 2-D models) and stored for similar regions. The resultant L/M/P may be stored in training databases 30A-30C or other storage areas.

Figure 3F:
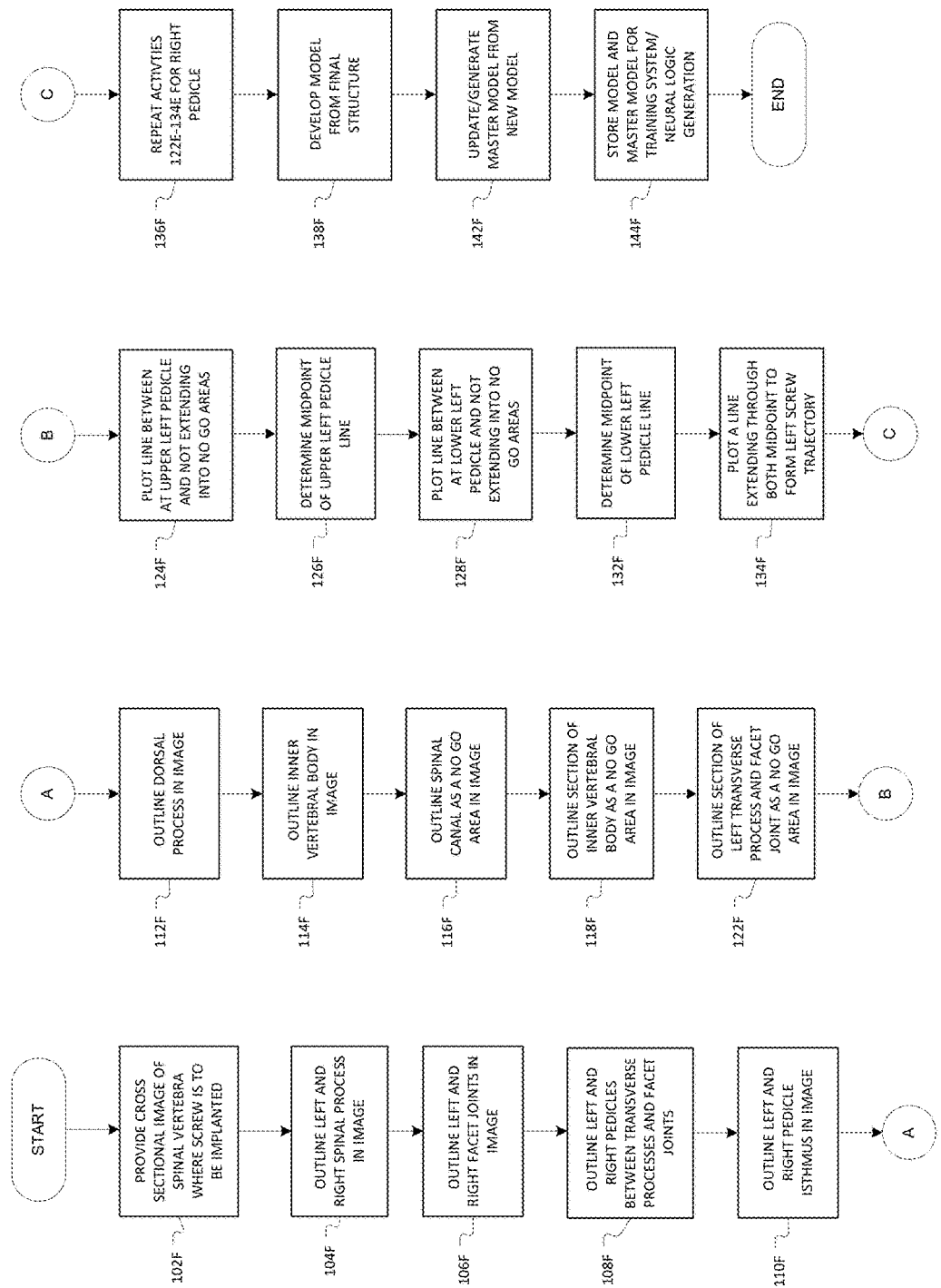
FIG. 3F is a flow diagram illustrating several methods for creating/employing a based logic/model/procedure (L/M/P) for an axial or cross sectional view of spinal vertebra from a computed tomography scan to be affected by an activity according to various embodiments.

In an embodiment, architecture 10 may include a display/touch screen display (317 FIG. 8), and one or more input devices (325 FIG. 8) that enable a User 70B to annotate image(s) 220A, 220B of sensor data 80A to identify physical landmarks, anatomical features, protected boundaries, and targets/access targets per activities 102E-110E of algorithm 100E and described in detail in algorithm 100F of FIG. 3F for an axial view of a L3 vertebrae. In an embodiment, architecture 10 (via training systems 30A-30C) may provide drawing tools and automatically detect landmarks, boundaries, and targets via a graphical processing unit (GPU 291) employing digital signal processing tools/modules/algorithms.

The GPU 291 may generate 3-D image(s) from two or more 2-D images 220A, 220B, in particular where two 2-D images 220A, 220B are substantially orthogonal in orientation. Architecture 10 may enable a User 70B via a display/touch screen display (317 FIG. 8) and one or more input devices (325 FIG. 8) to annotate 3-D image(s) representing an L3 vertebrae to identify physical landmarks, anatomical features, protected boundaries, and targets/access targets per activities 102E-110E of algorithm 100E.

FIG. 3F is a flow diagram illustrating several methods 100F for creating a based logic/model/procedure (L/M/P) for an axial view of a L3 vertebrae region to be affected by an activity according to various embodiments. FIGS. 4C to 4O include axial or cross sectional views 220C of spinal vertebra from a computed tomography scan including various segments of a L/M/P (220E FIG. 4P) being developed to determine target screw trajectories 189A, 189B for a vertebrae according to various embodiments via the methods 100F shown in FIG. 3F. FIGS. 4Q to 4W include sagittal or side views 220F of spinal vertebra from a computed tomography scan including various segments of a L/M/P (220G FIG. 4X) being developed to determine a target screw trajectory 189C for a L3 vertebrae per activities 102E-110E of algorithm 100E of FIG. 3E according to various embodiments.

As noted, algorithm 100F of FIG. 3F represents methods of forming a L/M/P 220E form an axial view of a vertebrae 256. It is noted that the order of the activities 102F to 122F may be varied. As noted in an embodiment, a User (medical professional or system expert) 70B may employ an interface (display 317, keyboard 325) via a training system 40A-40C or other system to create the L/M/P 220E shown in FIG. 4P via the algorithm 100F shown in FIG. 3F. In an further embodiment, the neural networks 50A-50C, training systems 40A-40C, or other machine learning system may create/form the L/M/P 220E via the algorithm 100E shown in FIG. 3E. In either embodiment, a cross-sectional image of a vertebra 220A generated by a sensor system 20A-20C may provide the initial basis for the creation/formation of a L/M/P 220E (activity 102F) including landmarks, boundaries, and one or more targets or access paths to targets.

Figure 4C:
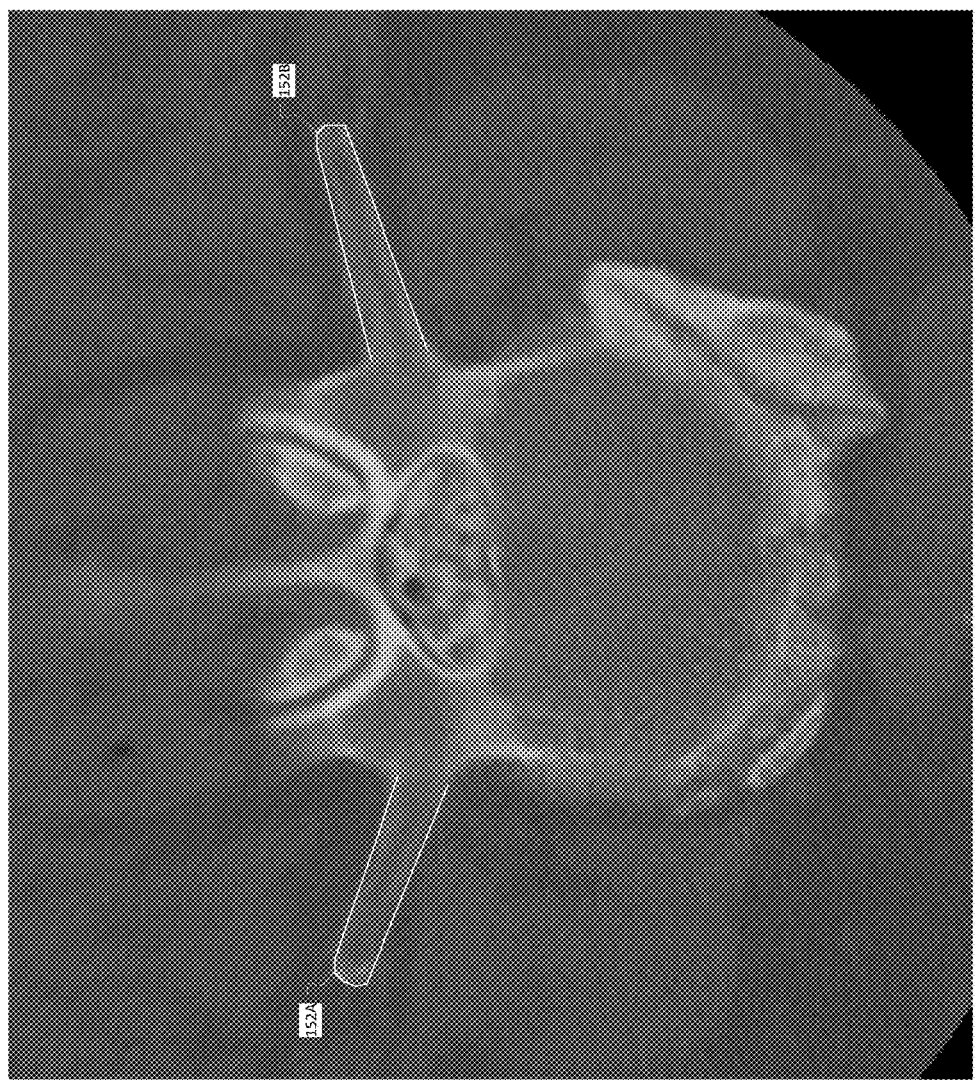
Figure 4D:
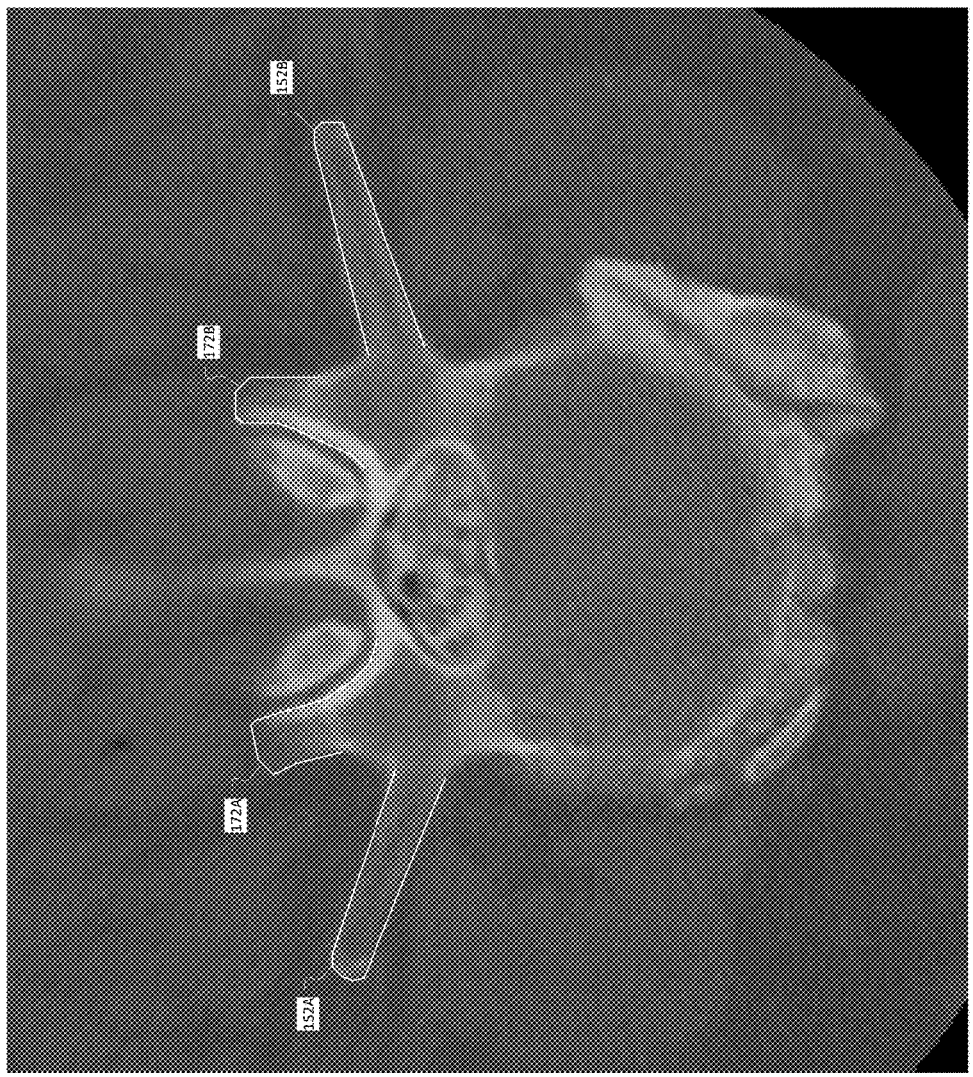
Figure 4E:
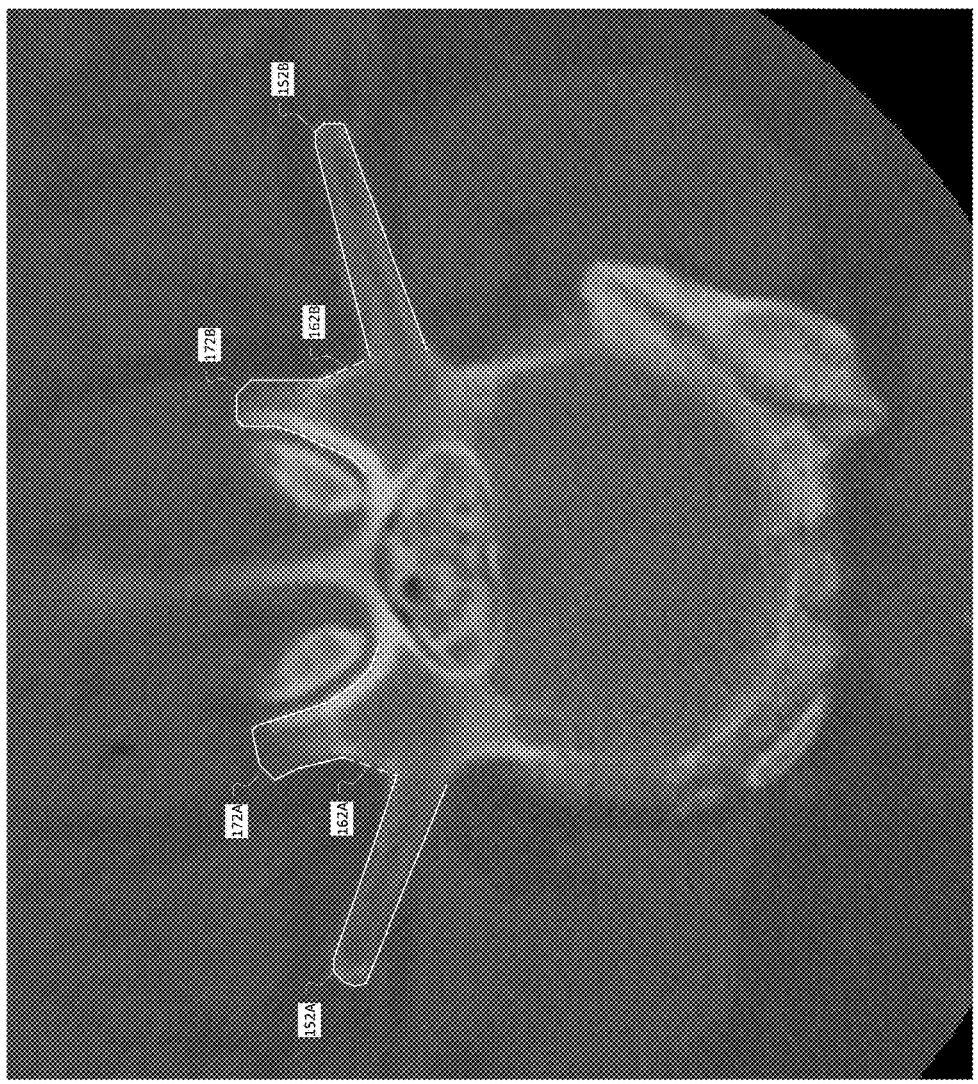
Figure 4F:
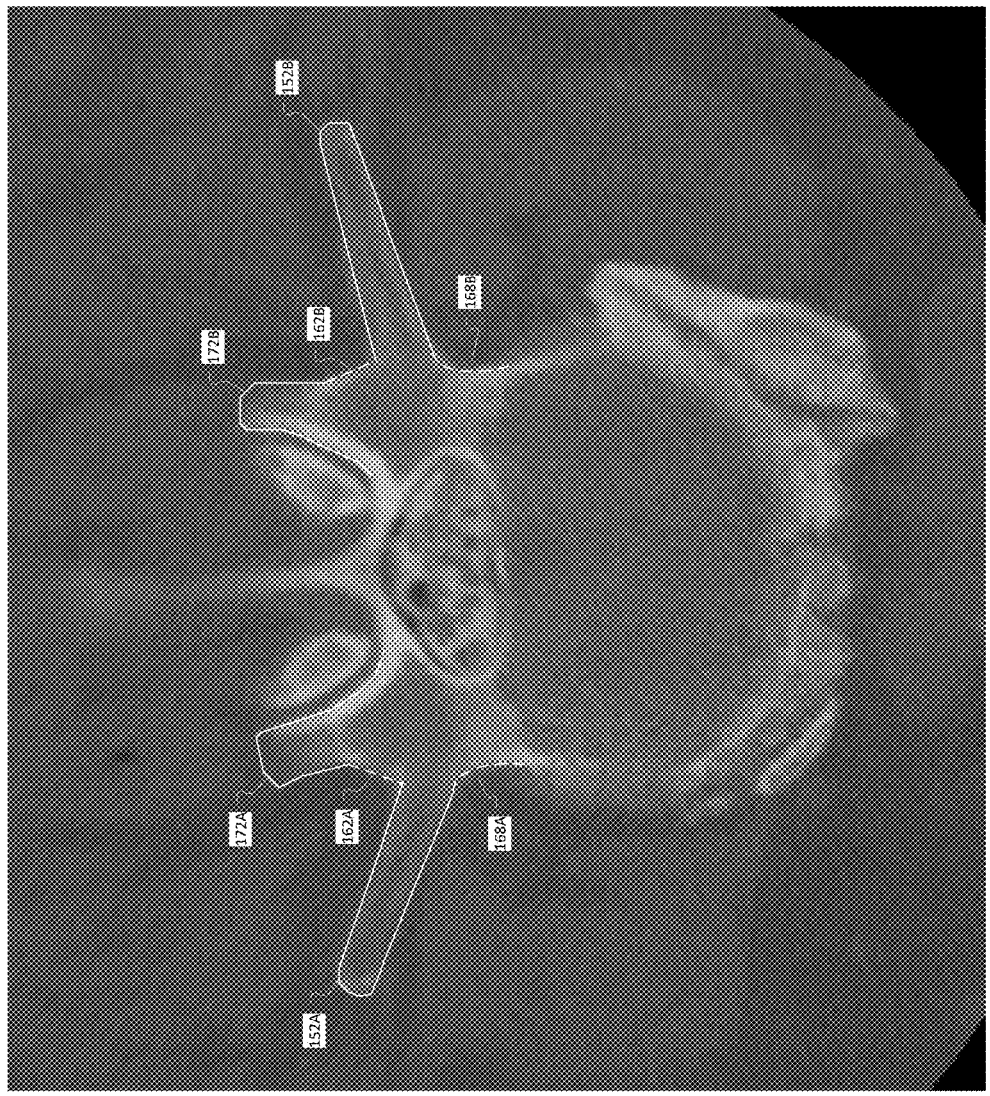

As shown in FIG. 4C, a User 70B, training system 40A-40C, or machine learning system (50A-50C), may create an outline 152A, 152B of the left and right transverse processes of a vertebrae (activity 104F) (representing a landmark 102E-FIG. 3E). In FIG. 4D, a User 70B, training system 40A-40C, or machine learning system (50A-50C), may create an outline 172A, 172B of the left and right facet joints of a vertebrae (activity 106F) (representing a landmark 102E-FIG. 3E). As shown in FIG. 4E, a User 70B, training system 40A-40C, or machine learning system (50A-50C), may create an outline 162A, 162B of the left and right upper pedicle of a vertebrae (activity 108F) (representing a landmark 102E-FIG. 3E). As shown in FIG. 4F, a User 70B, training system 40A-40C, or machine learning system (50A-50C), may create an outline 168A, 168B of the left and right pedicle isthmus of a vertebrae (activity 110F) (representing a landmark 102E-FIG. 3E).

Figure 4G:
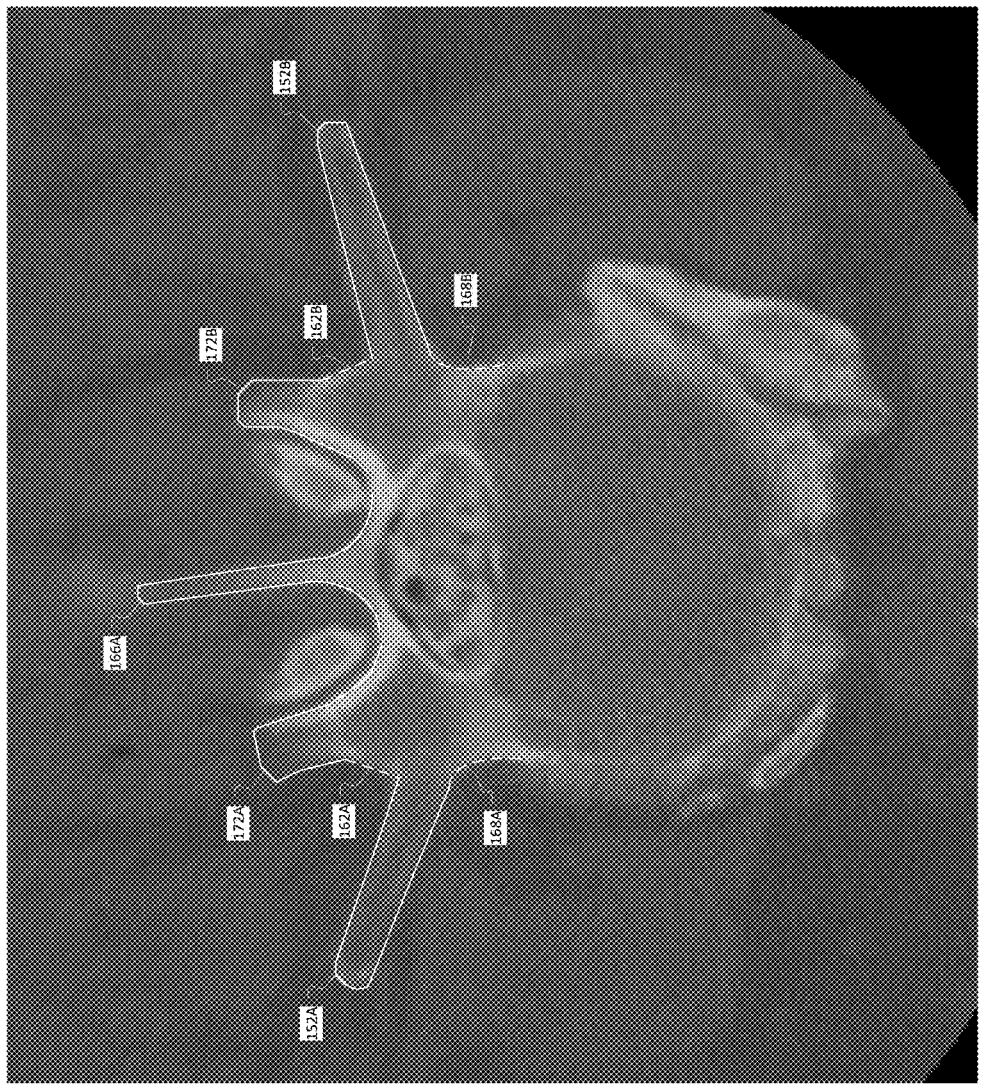
Figure 4H:
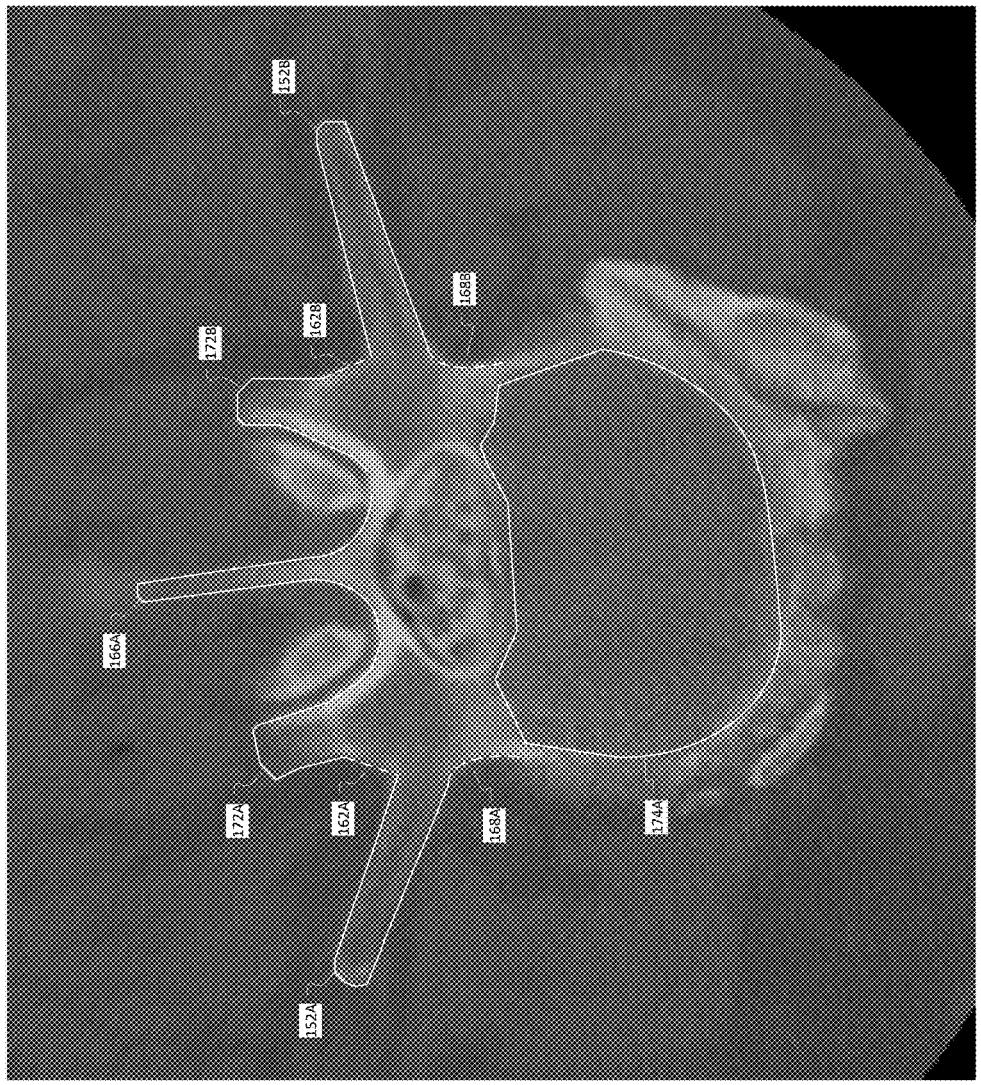
Figure 4I:
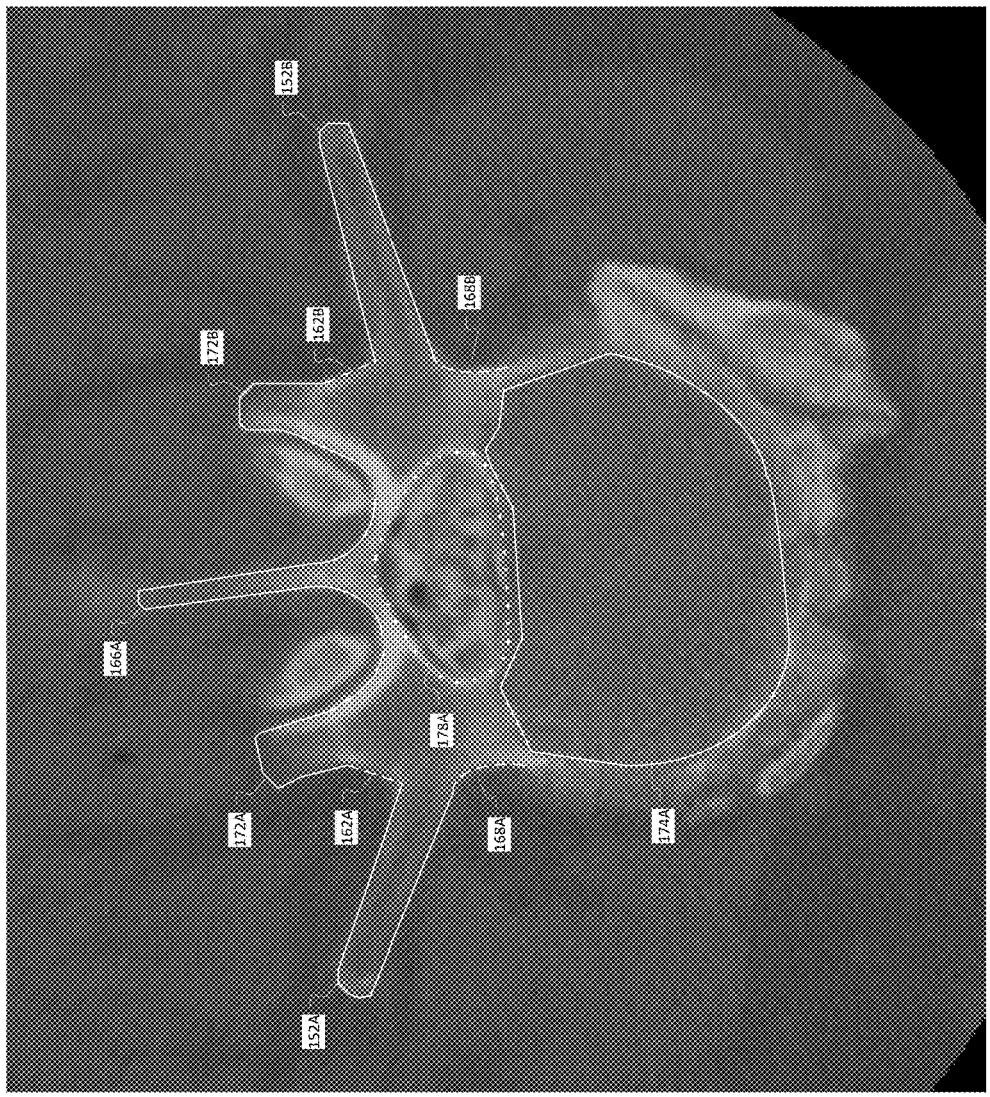
Figure 4J:
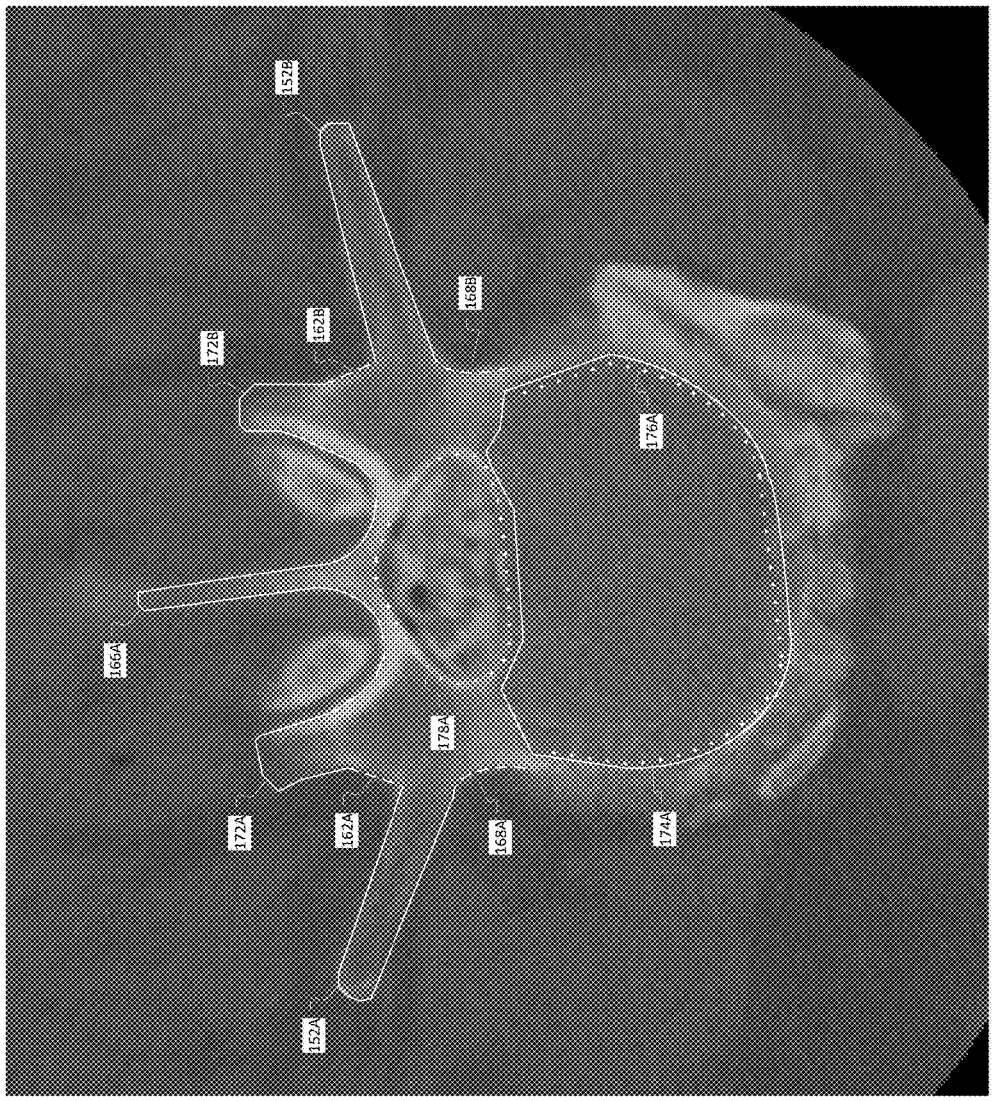

As shown in FIG. 4G, a User 70B, training system 40A-40C, or machine learning system (50A-50C), may create an outline 166A of the dorsal process of a vertebrae (activity 112F) (representing a landmark 102E-FIG. 3E). As shown in FIG. 4H, a User 70B, training system 40A-40C, or machine learning system (50A-50C), may create an outline 174A of the inner bony boundary of the vertebral body of a vertebrae (activity 114F) (representing a landmark 102E-FIG. 3E). As shown in FIG. 4I, a User 70B, training system 40A-40C, or machine learning system (50A-50C), may create an outline 178A of the spinal canal of a vertebrae (activity 116F) where this area or outline 178A is designated a no-go area (representing a boundary 104E-FIG. 3E). As shown in FIG. 4J, a User 70B, training system 40A-40C, or machine learning system (50A-50C), may create an outline 176A of a segment of inner bony boundary of the vertebral body of a vertebrae (activity 118F) where this segment or outline 176A is also designated a no-go area (representing a boundary 104E-FIG. 3E).

Figure 4K:
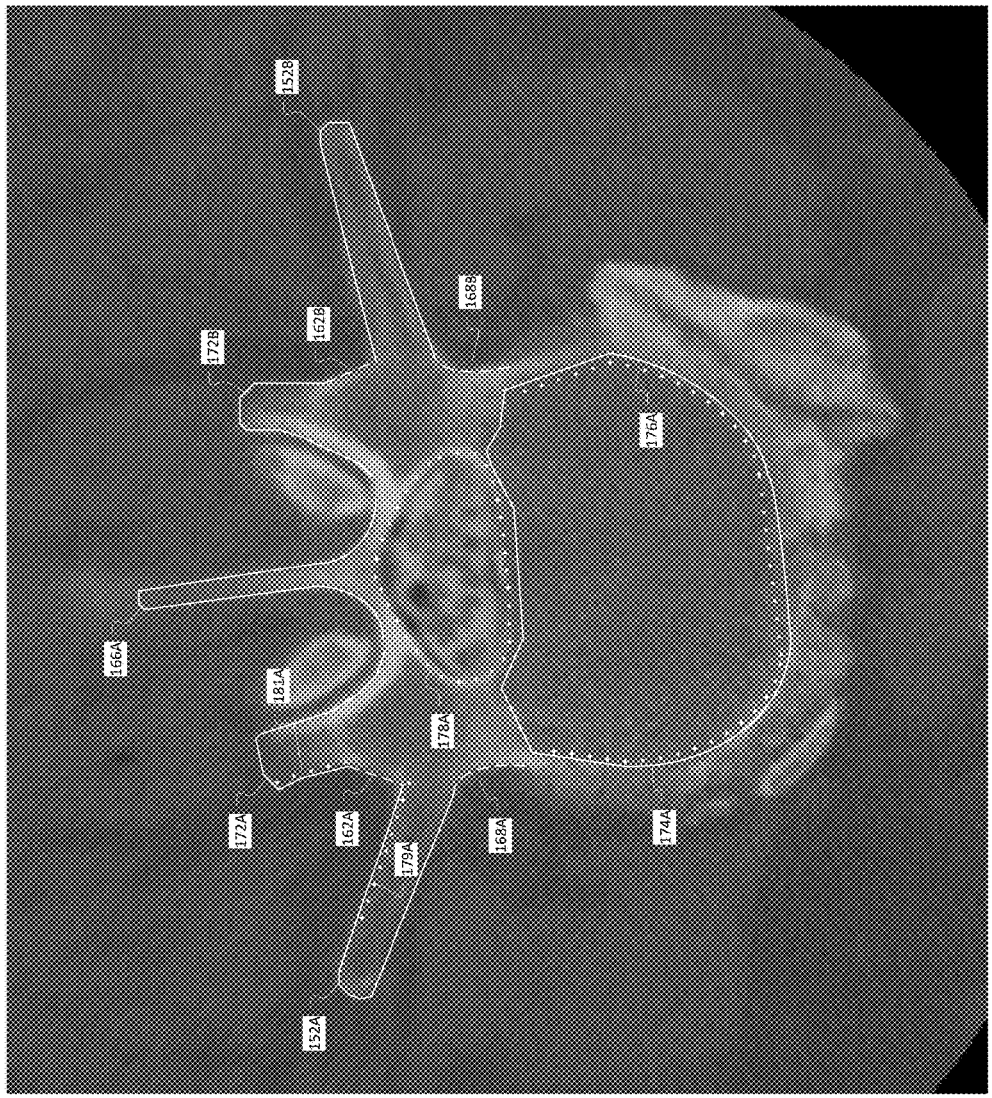
Figure 4L:
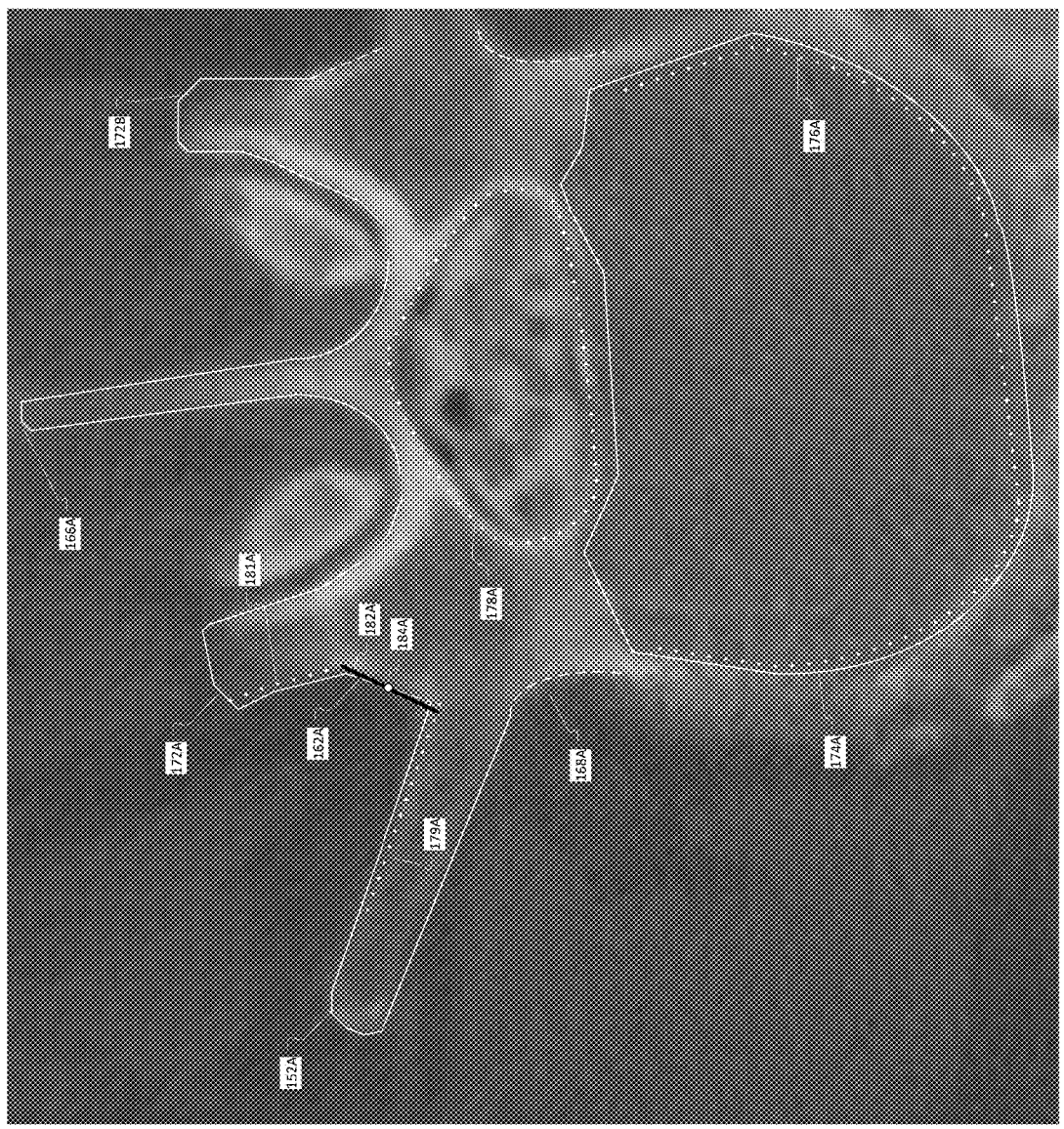

As shown in FIG. 4K, a User 70B, training system 40A-40C, or machine learning system (50A-50C), may create an outline 179A of a upper segment of the transverse process and an outline 181A of a left segment of a facet joint of a vertebrae (activity 118F) where the outlines 179A and 181A are also designated as no-go areas (representing a boundary 104E-FIG. 3E). As shown in FIG. 4L, based on the created outlines 152A-178A, a User 70B, training system 40A-40C, or machine learning system (50A-50C), may plot a line 182A between the transverse process outline 152A and facet joint 172A along upper pedicle outline 162A but not in designated no-go areas or outlines 179A, 181A (activity 124F) and determine the midpoint 184A of the line 182A (activity 126F) (determining targets or access 108E-FIG. 3E).

Figure 4M:
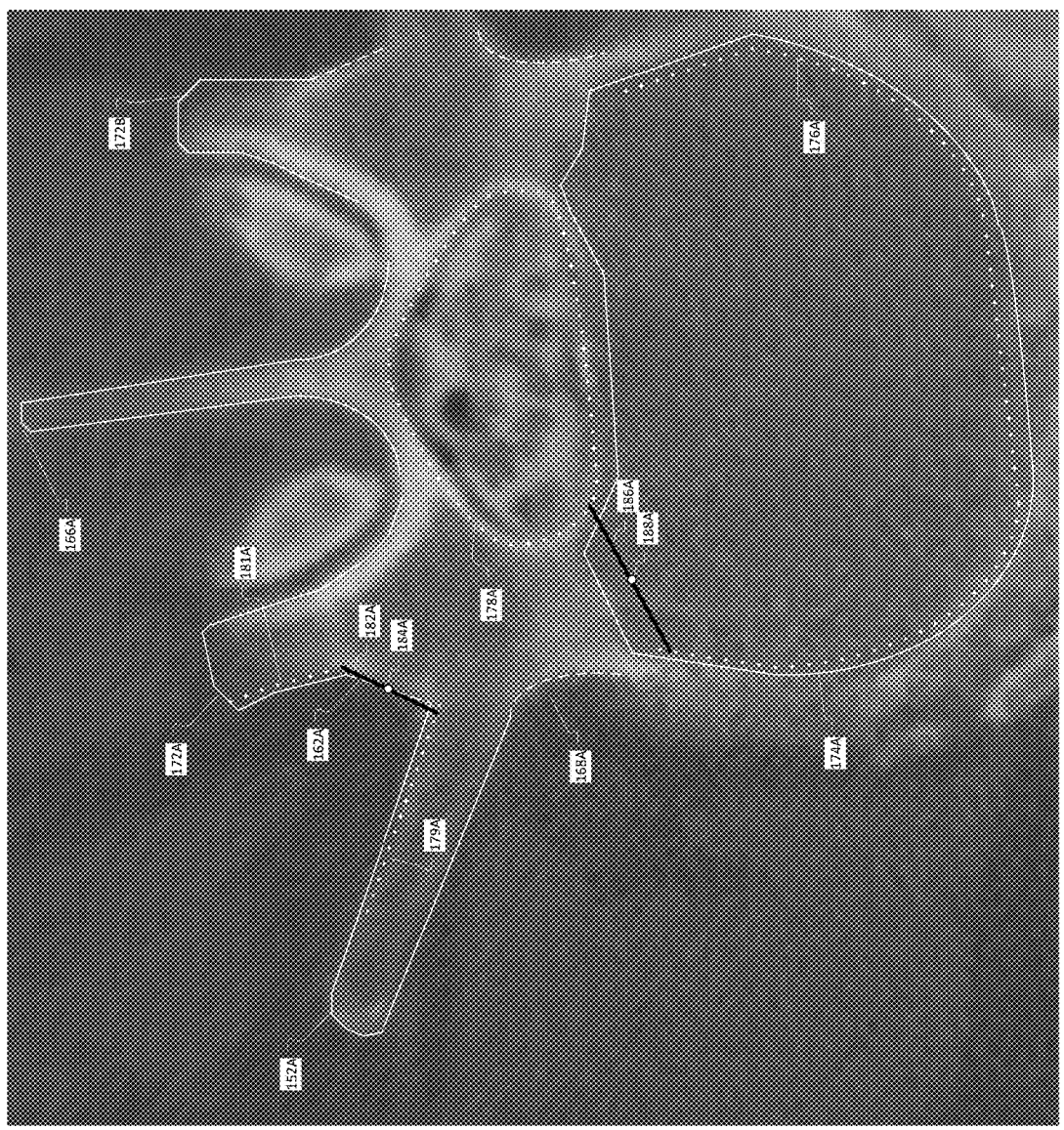
Figure 4O:
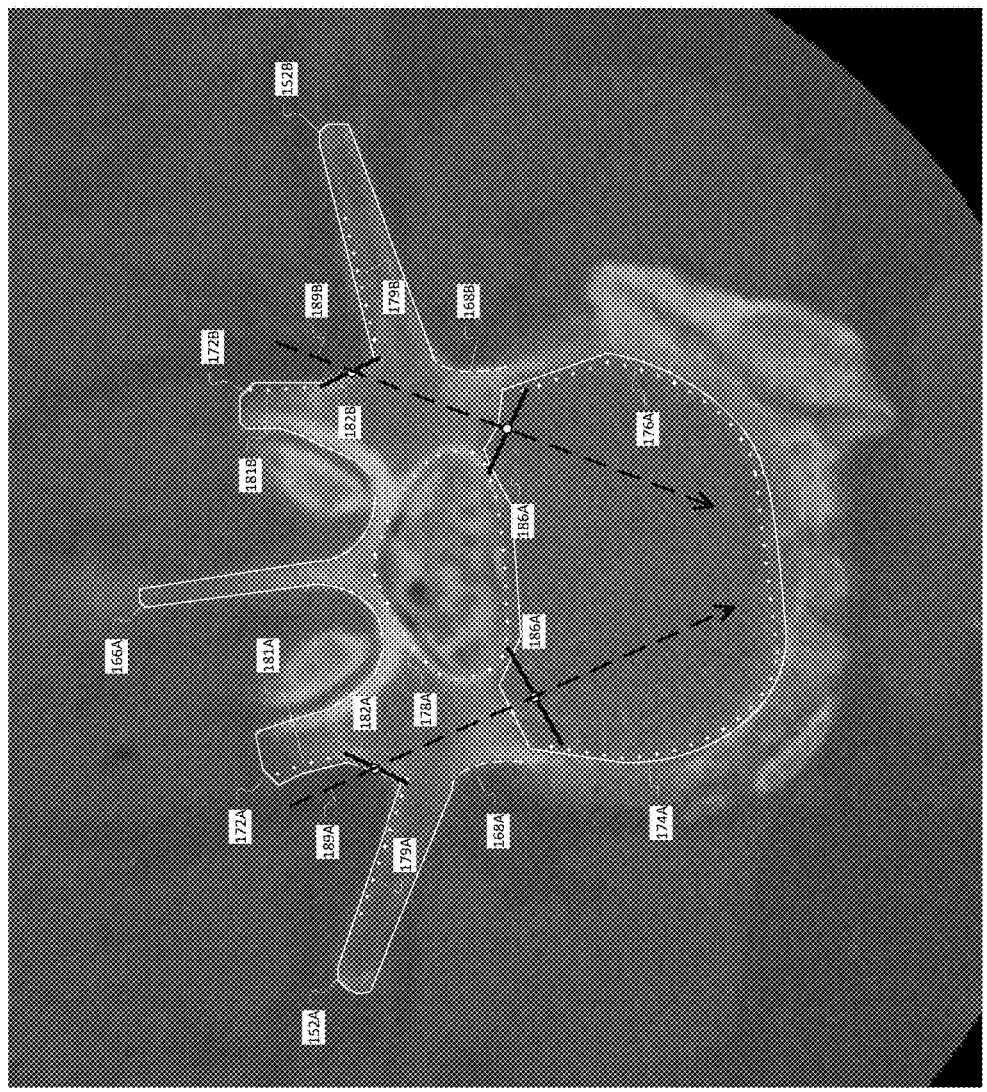

Similarly, as shown in FIG. 4M, based on the created outlines 152A-178A, a User 70B, training system 40A-40C, or machine learning system (50A-50C), may plot a second line 186A along the lower pedicle in the vertebral body outline 174A and between the designated no-go areas or outlines 176A and 178A (activity 128F) and determine the midpoint 188A of the line 186A (activity 132F) (determining targets or access 108E-FIG. 3E). As shown in FIG. 4N, a User 70B, training system 40A-40C, or machine learning system (50A-50C), may plot a left pedicle screw trajectory line 189A between the midpoints 184A, 188A of the lines 184A, 186A (activity 134F) (determining targets or access 108E-FIG. 3E). The activities 122F to 134F may be repeated for the right pedicle to outline the no-go areas 179B, 181B, plot the lines 182B and 186B, determine their midpoints, and plot the right pedicle screw trajectory line 189B as shown in FIG. 4O (activity 136F).

Figure 4P:
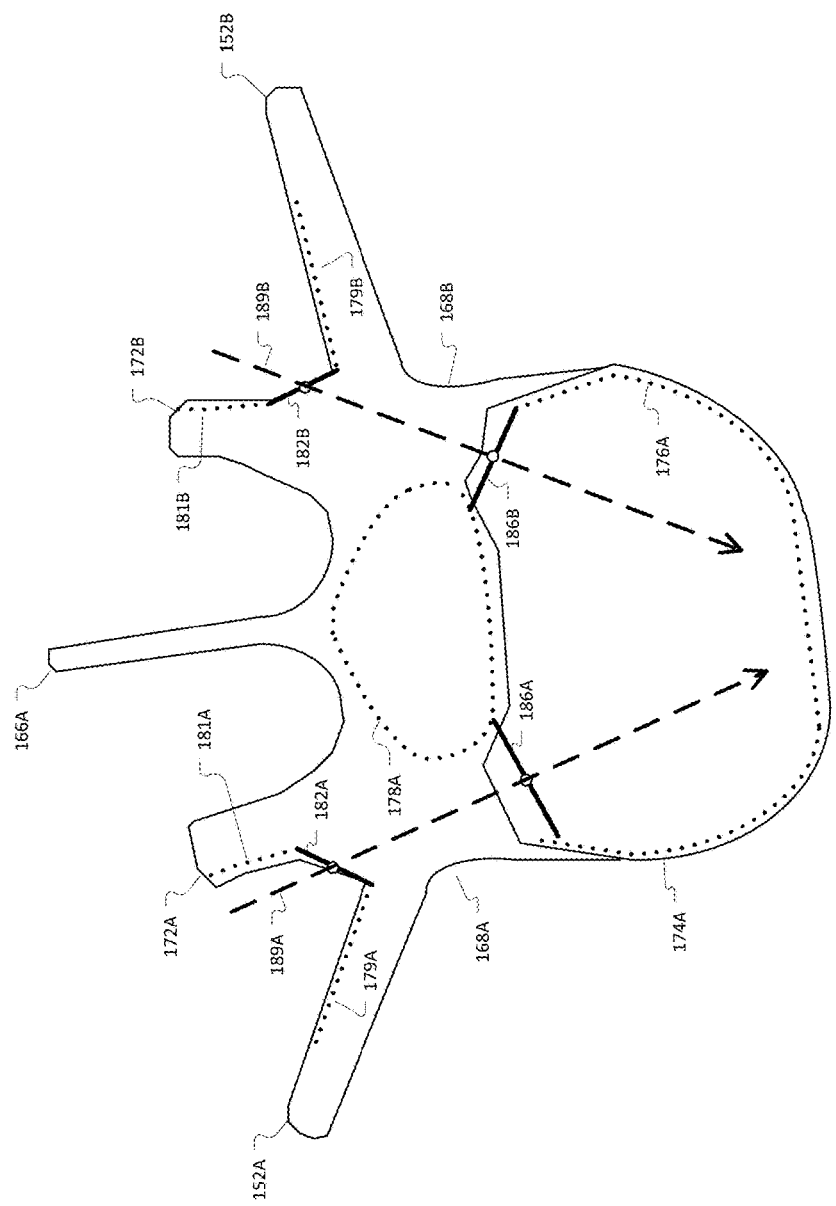
FIG. 4P is an axial or cross sectional view of a spinal vertebra model with targets/annotations according to various embodiments.

As shown in FIG. 4P, a User 70B, training system 40A-40C, or machine learning system (50A-50C), may form the final L/M/P 220E (activity 138F) (form the model 110E-FIG. 3E). In an embodiment, a training system 40A-40C, or machine learning system (50A-50C), may generate, update, or create multiple L/M/P 220E to be employed by architecture 10 when performing or learning the same activity (activity 142F) and store the L/M/P 220E (activity 144F) (form the model 110E-FIG. 3E). Once the I/M/P 202E is created it may be used to train neural networks 50A-50C to determine the desired screw trajectories 189A, 189B based on received sensor data 80A.

Figure 4Q:
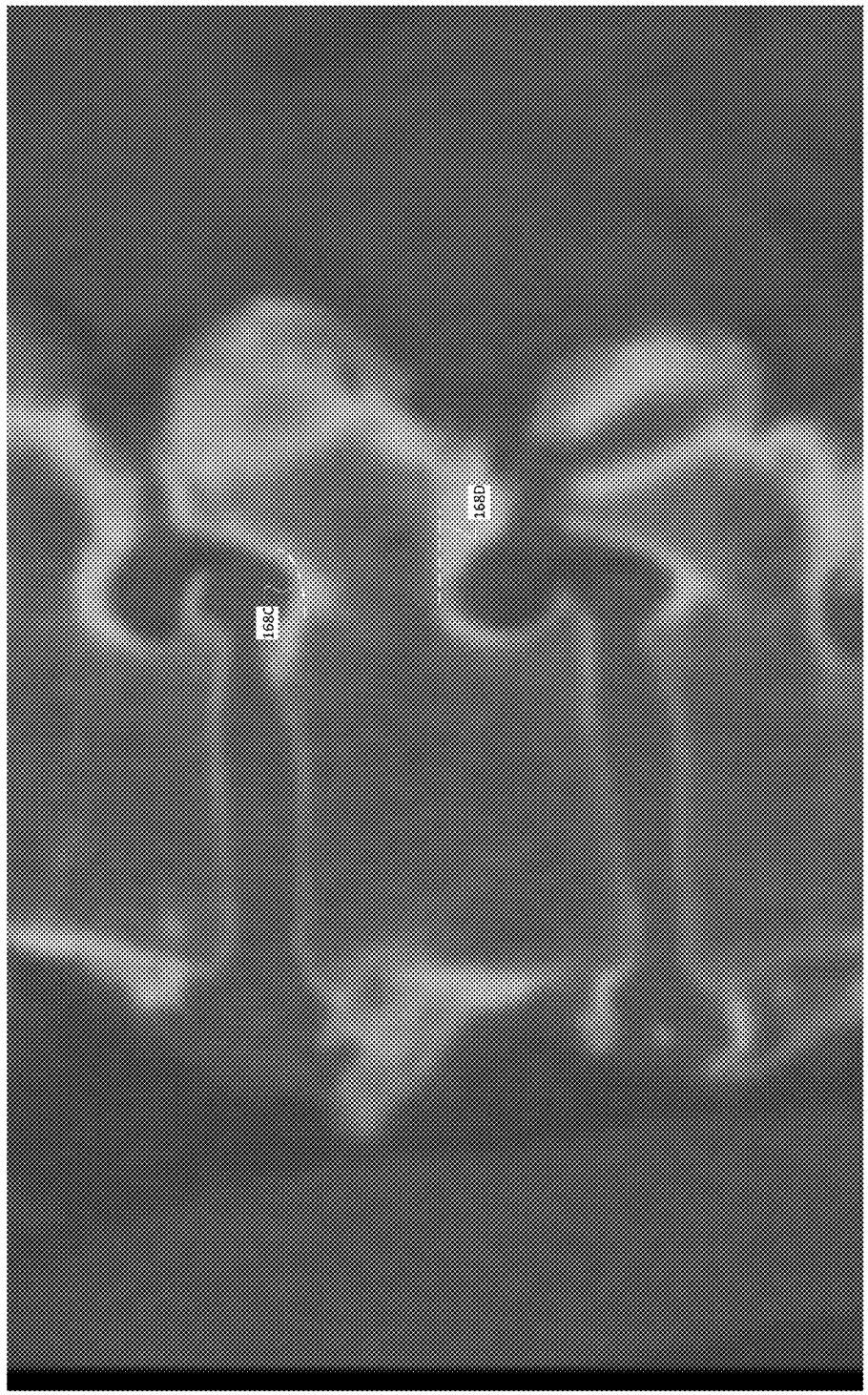
Figure 4R:
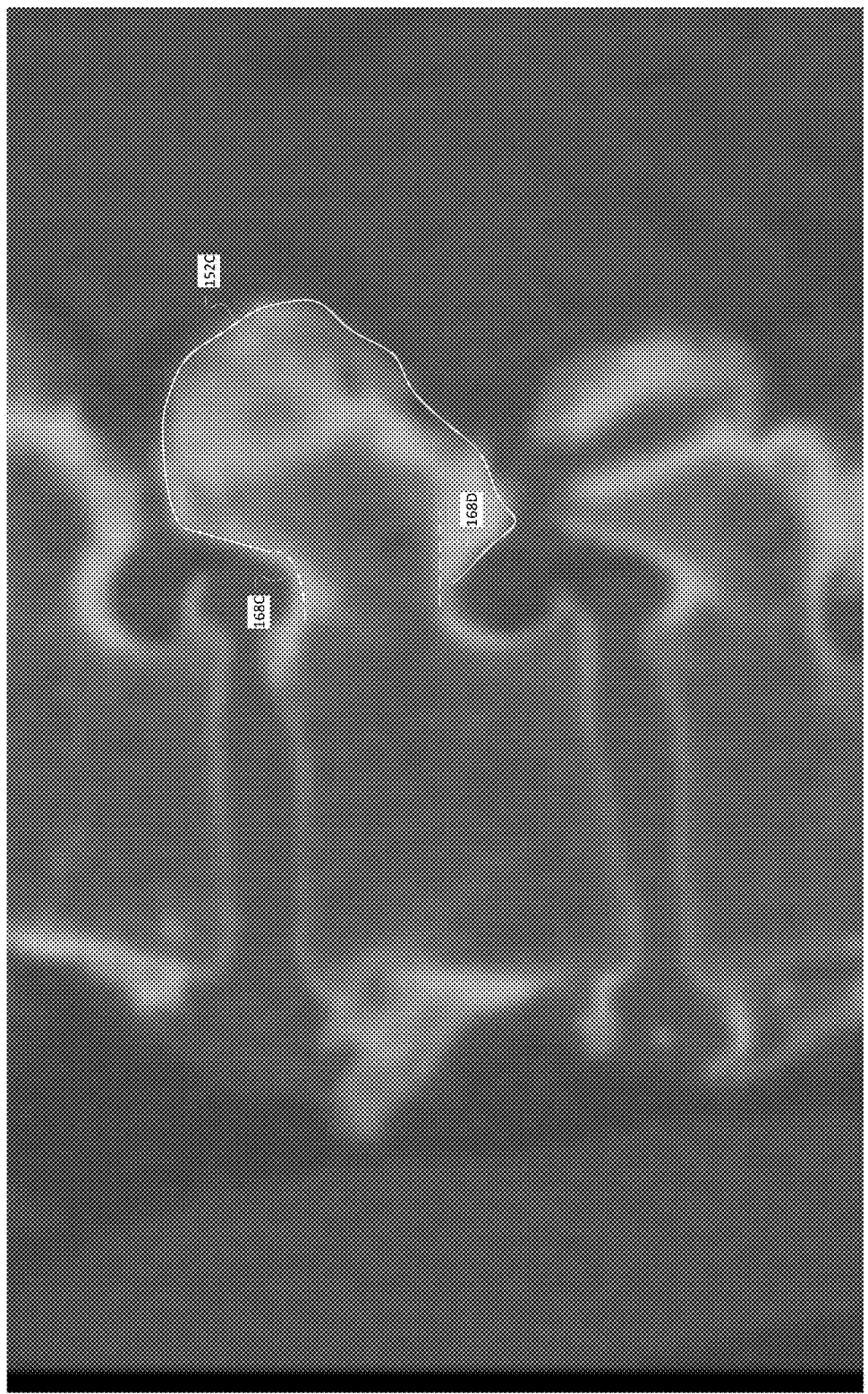

As noted, FIGS. 4Q to 4W include sagittal or side views 220F of spinal vertebra from a computed tomography scan including various segments of a L/M/P (220G FIG. 4X) being developed to determine a target screw trajectory 189C for a L3 vertebrae per activities 102E-110E of algorithm 100E of FIG. 3E according to various embodiments. In particular, as shown in FIG. 4Q, a User 70B, training system 40A-40C, or machine learning system (50A-50C), may create outlines 168C, 168D of upper and lower pedicle isthmus of a L3 vertebrae 256 (representing a landmark 102E-FIG. 3E). As shown in FIG. 4R, a User 70B, training system 40A-40C, or machine learning system (50A-50C), may create an outline 152C of a right transverse process of a L3 vertebrae 256 (representing a landmark 102E-FIG. 3E).

Figure 4S:
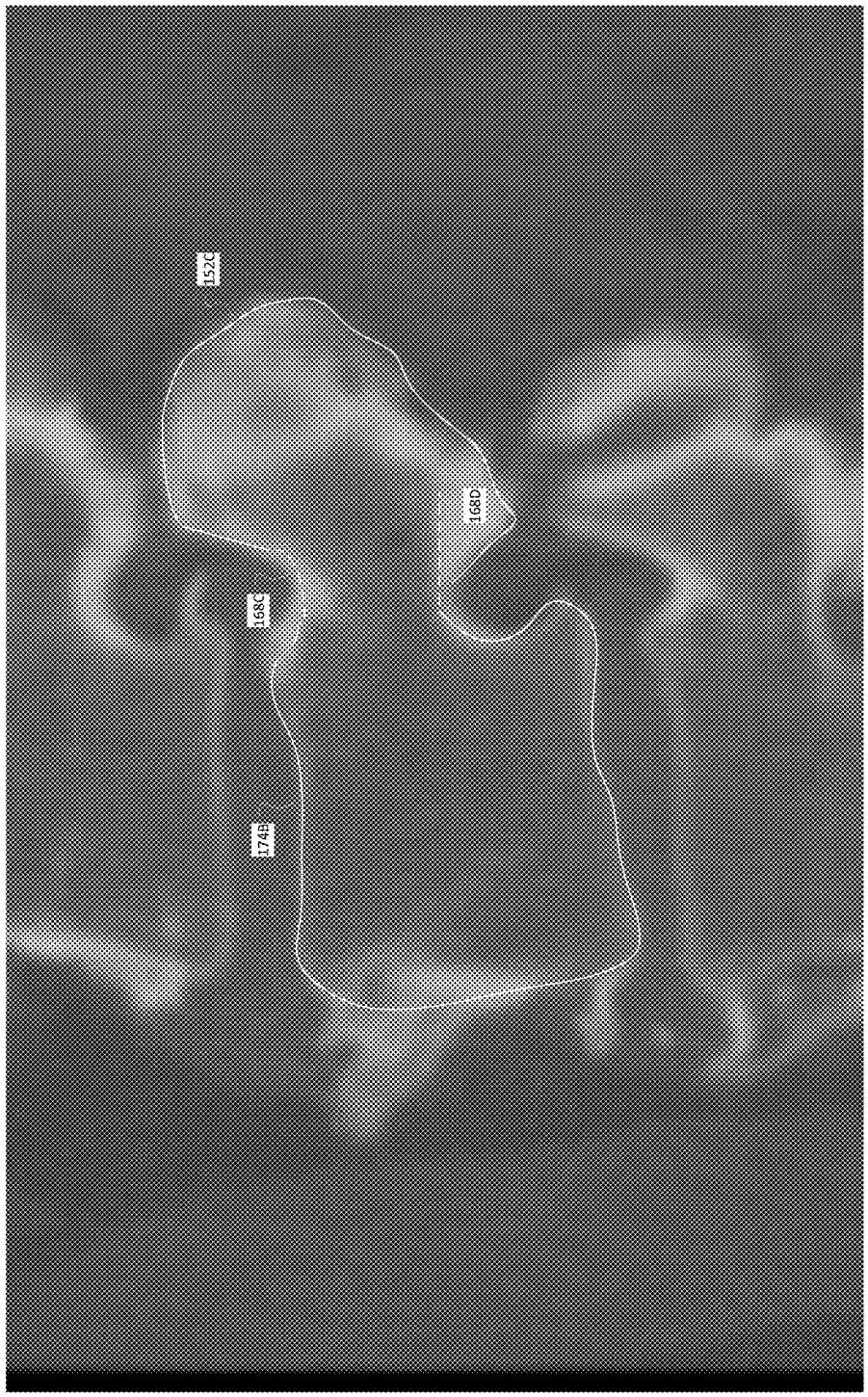
Figure 4T:
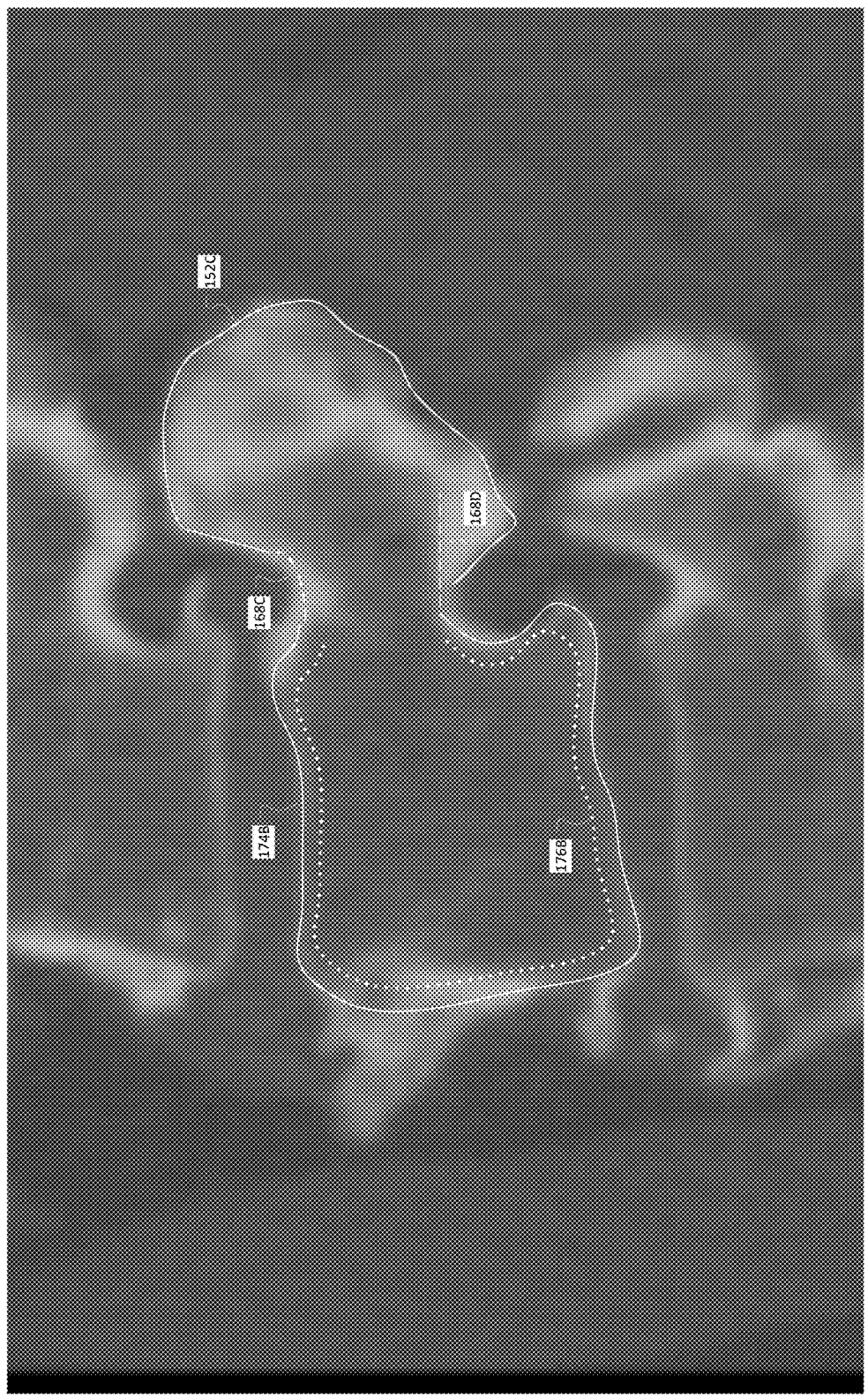

As shown in FIG. 4S, a User 70B, training system 40A-40C, or machine learning system (50A-50C), may create outline 174B of the cortex of a L3 vertebrae 256 (representing a landmark 102E-FIG. 3E). As shown in FIG. 4T, a User 70B, training system 40A-40C, or machine learning system (50A-50C), may create an inner boundary outline 176B offset from the cortex of a L3 vertebrae 256 (representing a boundary 104E-FIG. 3E). The boundary outline 176B may be created to prevent vertebrae wall compromise in an embodiment.

Figure 4U:
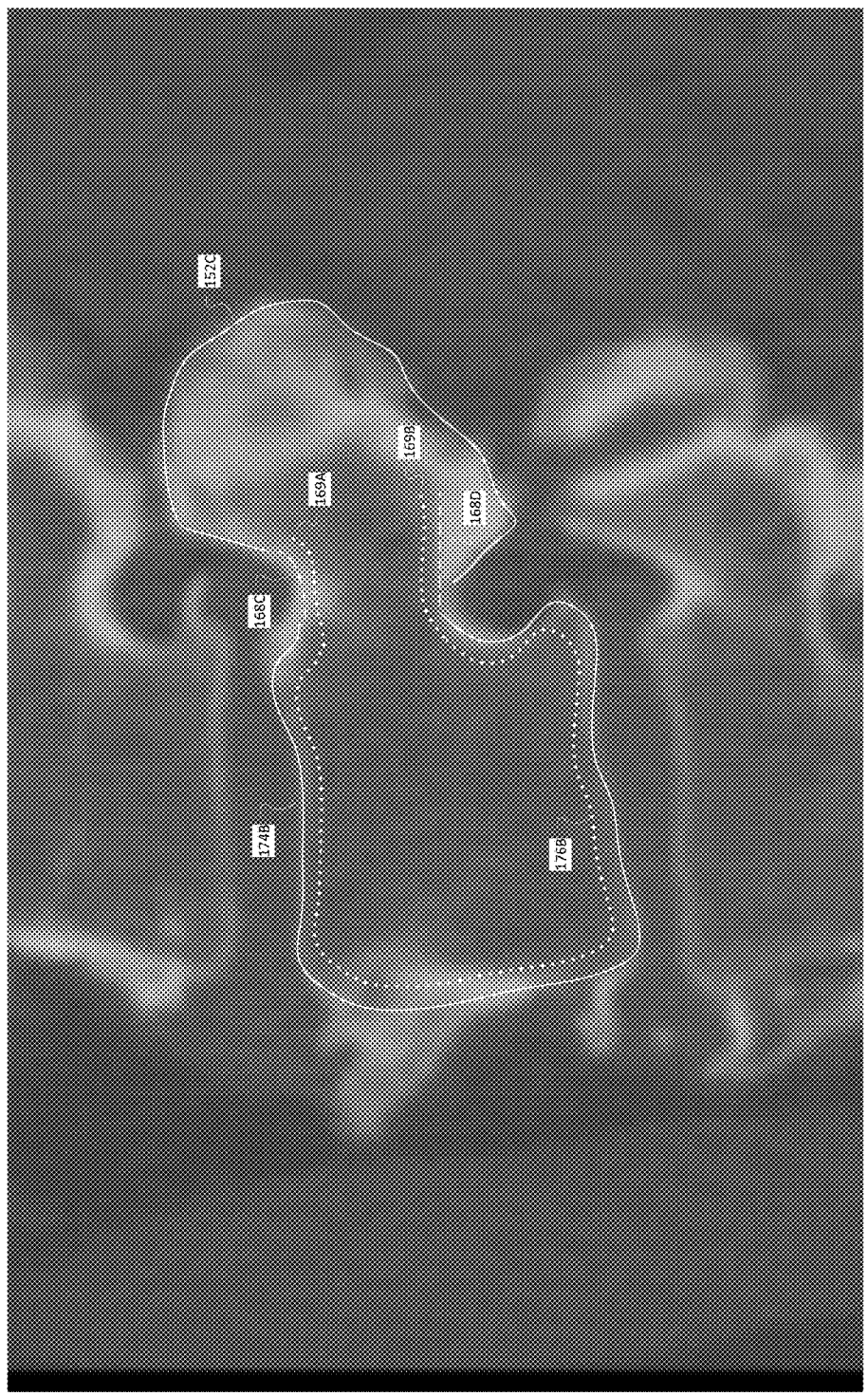
Figure 4V:
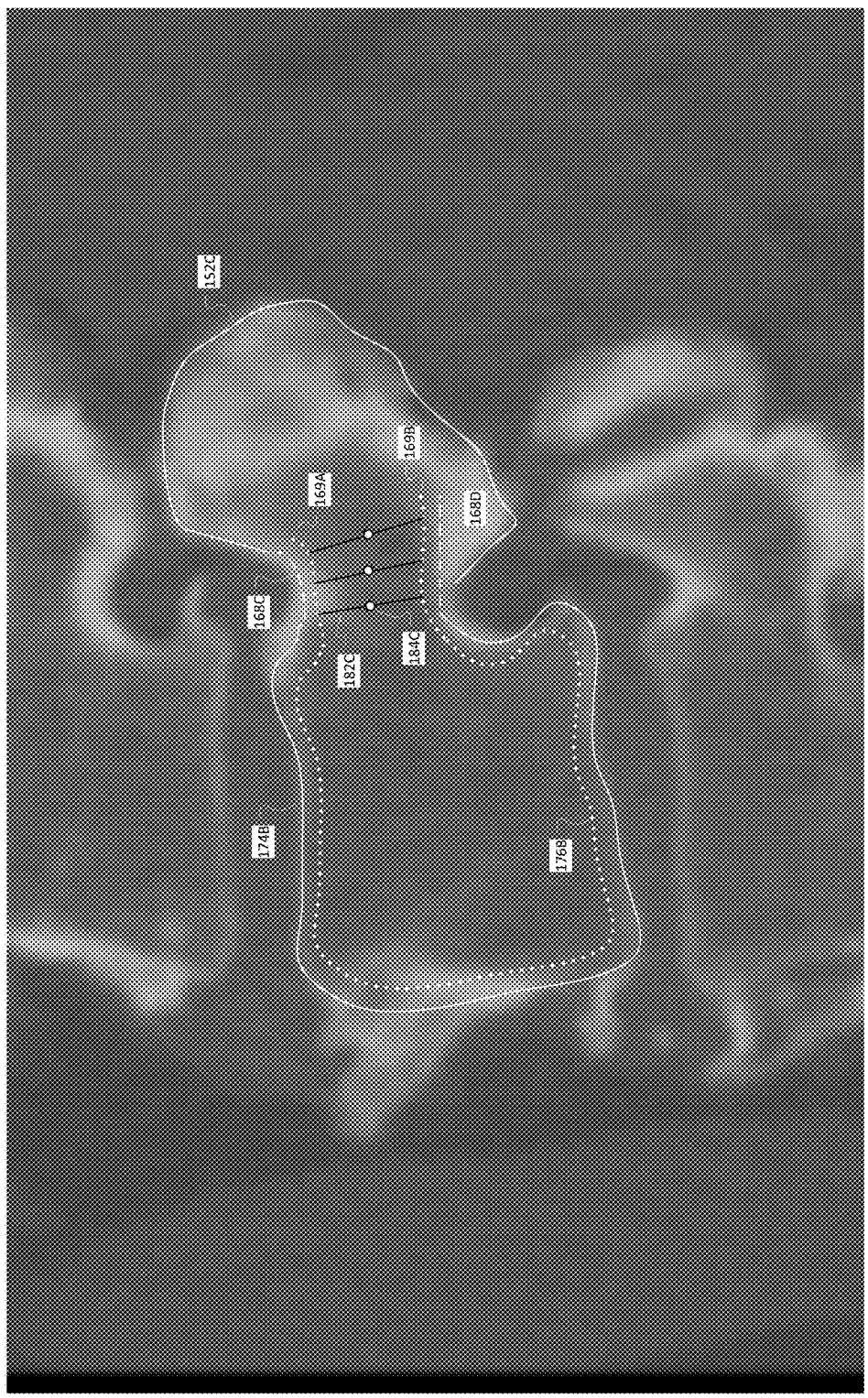

As shown in FIG. 4U, a User 70B, training system 40A-40C, or machine learning system (50A-50C), may create inner boundary outlines 169A, 169B inset from the upper/lower pedicle isthmus 168C, 168D of a L3 vertebrae 256 (representing a boundaries 104E-FIG. 3E). The boundaries outlines 169A, 169B may be created to prevent pedicle wall compromise in an embodiment. As shown in FIG. 4V, a User 70B, training system 40A-40C, or machine learning system (50A-50C), may plot two or more vertical lines 182C between the boundaries outlines 169A, 169B of the upper/lower pedicle isthmus 168C, 168D of a L3 vertebrae 256 and determine their midpoints 184C (determining targets 106E-FIG. 3E).

Figure 4X:
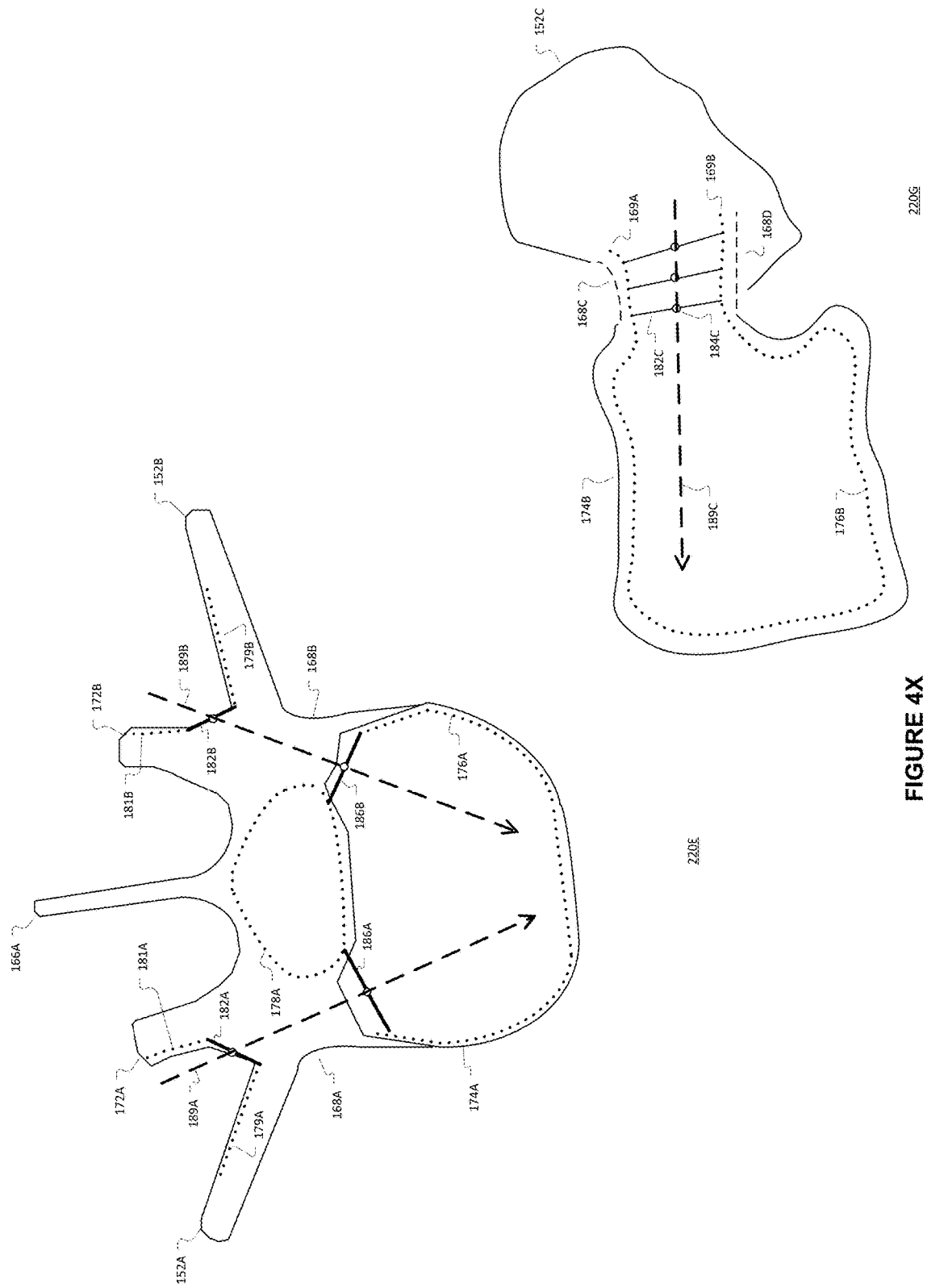
FIG. 4X is an axial or cross sectional view of a spinal vertebra model with targets/annotations and a sagittal or side view a spinal vertebra model with targets/annotations according to various embodiments.

As shown in FIG. 4W, a User 70B, training system 40A-40C, or machine learning system (50A-50C), may plot a right pedicle screw trajectory line 189A between the midpoints 184C, 188A of the lines 184C (determining targets or access 108E-FIG. 3E). The combination of the landmark, boundary, and targeting activities may yield the transverse L3 vertebrae model 220G shown in FIG. 4X. The axial model 220E for the L3 vertebrae is also shown in FIG. 4X for reference. A training system 40A-40C or machine learning system (50A-50C) may create a 3-D right pedicle screw trajectory line based on the axial view screw trajectory 189B and sagittal view screw trajectory 189C.

The resultant model(s) or L/M/P 220E, 220G may be stored in a database such a training database 30A-30C in an embodiment for use for a current activity or future activities. The stored models may be categorized by the associated region or region(s) (activity 110E—FIG. 3E). As noted, algorithm 100E may determine whether one or more models (L/M/P) exist in activity 101E prior to creating or forming one or more models (L/M/P) for a region to be affected by an activity. If one or more models (L/M/P) exist for a region to be affected by an activity, a models (L/M/P) may be retrieved (activity 112E) and compared/correlated to current, related sensor data 80A for a region (activity 114E) to determine if the model is similar enough to the current region to be employed for the current activity (activity 116F).

In an embodiment, a training system 40A-40C or neural network system 60A-60C may enlarge, shrink, and shift models (L/M/P) up/down to attempt to match landmarks in the models (L/M/P) with the image represented by current sensor data 80A. When the image represented by current sensor data 80A is sufficiently correlated with the model's landmarks, the model L/M/P may be used to determine/verify targets or access to targets (activity 124E). In an embodiment, the model may be updated and stored based on the verified or determined targets or access to targets (activity 126E).

In an embodiment, current sensor data 80A is sufficiently correlated with the model's landmarks when the combined error (differential area versus integrated total area represented by landmarks in an embodiment) is less than 10 percent. When image represented by current sensor data 80A is not sufficiently correlated with the retrieved model's landmarks, another model for the region may be retrieved if available (activities 118E, 122E). If another model for the region is not available (activity 118E), a new model may be formed (activities 102E-110E).

Figure 5A:
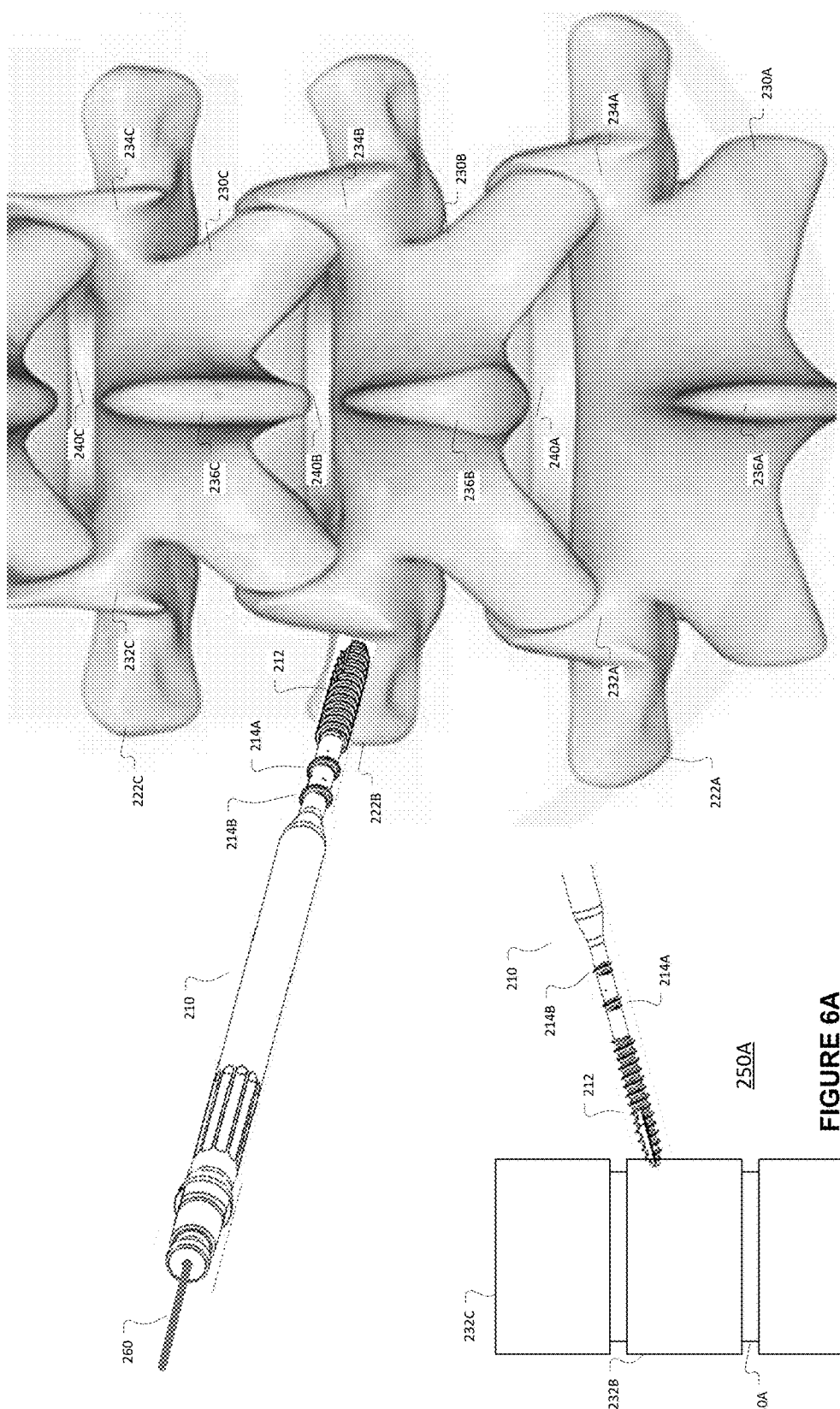

Once the screw trajectories 189A, 189B are determined, architecture 10 employ the trajectories in a medical procedure including inserting a pedicle screw along a trajectory 189A, 189B. For the next activity or step of a procedure, another I/M/P 220E may be formed to be used with neural networks 50A-50C to control the operation of one or more robots 60A-60C with sensor data 80A. For example, architecture 10 could be employed to insert a tap 210 as shown in FIG. 5A into a pedicle along the trajectory 189A, 189B. As shown in FIG. 5A, a tap 210 may include a tapping section 212 with two offset depth indicators 214A, 214B where the tapping section 212 has a known outer diameter.

A medical professional 70B may select a tap 210 having a desired outer diameter to create a bony tap in a pedicle 232 based on the pedicle size. Architecture 10 may also select a tap having a optimal diameter based on measuring the pedicle 232 dimensions as provided by one or more sensor systems 20A-20C. The neural network systems 50A-50C may direct a robotic system 60A-60C to select a tap having an optimal outer tapping section 212 diameter. The taps 210 may have markers 214A, 214B that a sensor system 20A-20C may be able to image so one or more neural network systems 50A-50C may be able to confirm tap selection where the neural network systems 50A-50C may direct sensor system(s) 20A-20C to image a tap 210.

During training activities (108A and 112A of FIG. 3A), one or more sensor system's 20A-20C data (generated, received, and position) may be sampled at an optimal rate as a medical professional 70B initially places a tap 210 tapping section 212 against a pedicle 232 along a desired pedicle screw trajectory 234A and continues to advance the tap 210 to a desired depth within a vertebra 230A body 244 as shown in FIGS. 5B, 6B, 5C, and 6C. As shown in these figures, a tap 210 may include one or more radiographically visible markers 214A, 214B in addition to the tapping section 212 having known locations on the tap 210 distal end. One or more neural network systems 50A-50C may be trained to determine the tap depth via live sensor data 80A provided by one or more sensor systems 20A-20C to determine the idea tap depth within a vertebra 230A.

Figure 6A:
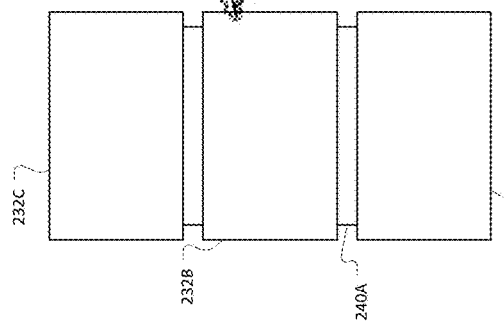
Figure 5C:
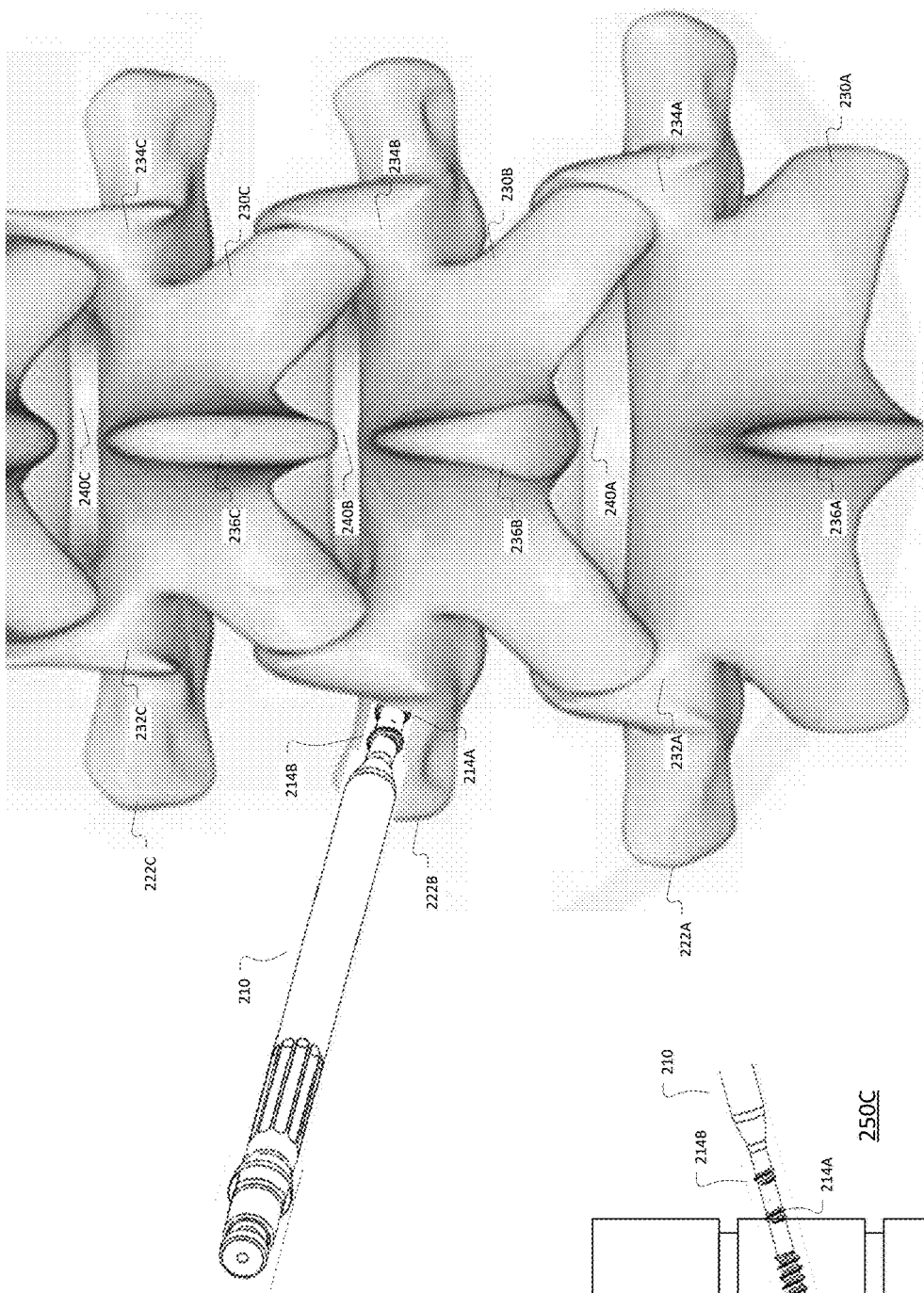
Figure 6C:
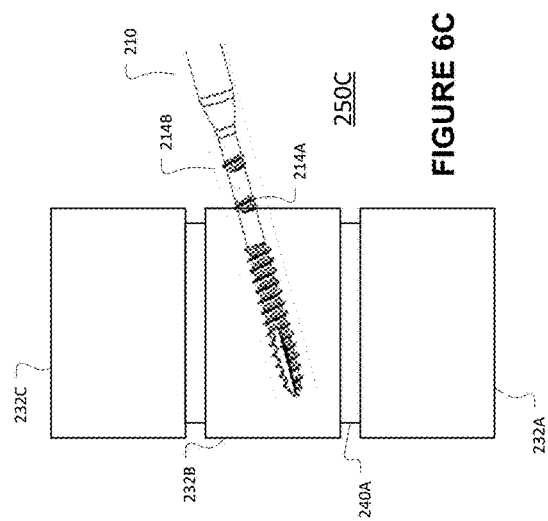
Figure 5D:
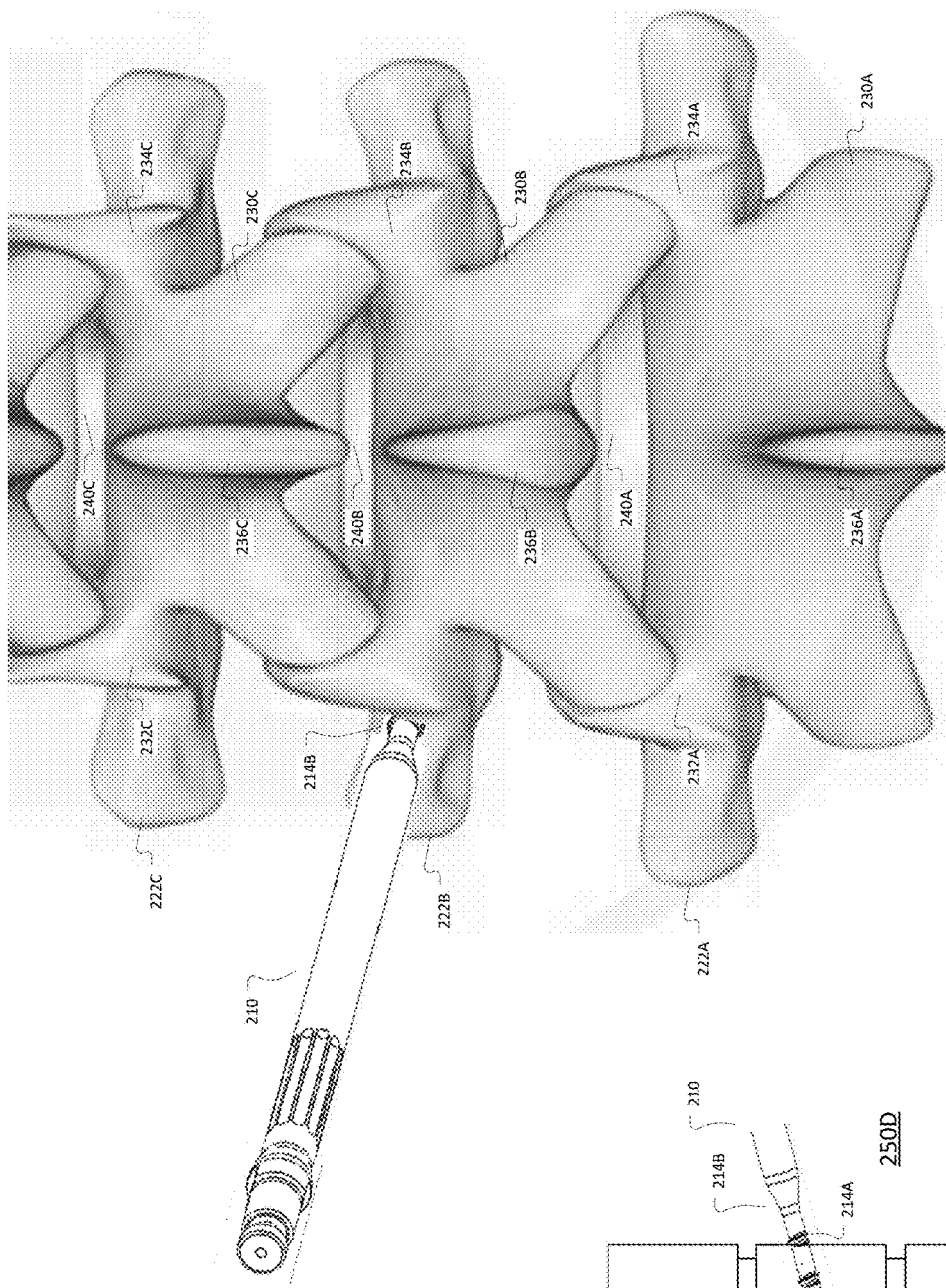
Figure 6D:
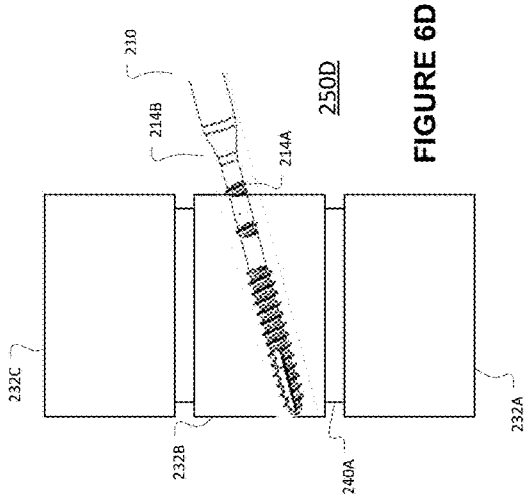

In an embodiment, a medical professional 70B may also train architecture 10 on improper tap 210 usage as shown in FIGS. 5D and 6D. Neural network systems 50A-50C may be trained via training systems 40A-40C on undesired results in addition to desired results. As shown in FIGS. 5D and 6D, a tap 210 distal end has been advanced too far into a vertebra 230A and violated its vertebral cortex 246. The same logic could be applied to a self-tapping pedicle screw 270C in an embodiment. It is noted that the training activities could be performed on spinal models or cadavers so architecture 10 can be trained to avoid adverse or unwanted results in addition to desired results or activities.

In the activity, once the tap 210 has been advanced to a desired depth as shown in FIGS. 5C and 5D, a medical professional 70B may remove the tap 210 and implant a pedicle screw 270C having an optimal diameter and length as shown in FIGS. 5E and 6E. As shown in FIGS. 7A to 7D, pedicle screws 270A to 270D have shafts 274A to 274D with a common diameter but different lengths (35 mm, 40 mm, 45 mm, and 50 mm, respectively in an embodiment). A medical professional may select a pedicle screw 270C having the maximum diameter and length that will be insertable into a pedicle 232 and not violate a vertebra's 230A cortex when fully implanted.

A neural network systems 50A-50C may be trained to select a pedicle screw 270A-270D having an optimal diameter and length based on sensor data 80A provided by one or more sensor systems 20A-20C (under a neural network system's 50A-50C direction in an embodiment) based on one or more developed I/M/P. It is noted that during the deployment of the tap 210 or a pedicle screw 270A-D, other sensor data 80A from many different sensor systems 20A-20C may be employed, trained, and analyzed to ensure a tap 210 is properly deployed and a pedicle screw 270A-D is properly implanted. Sensor systems 20A-20C may include electromyogram "EMG" surveillance systems that measure muscular response in muscle electrically connected near a subject vertebra 230A where the architecture 10 may be trained to stop advancing a tap 210 or pedicle screw 270A-D as a function of the EMG levels in related muscle. A sensor system 20A-20C may also include pressure sensors that detect the effort required to rotate a tap 210 or pedicle screw 270A-D where the architecture 10 may be trained to prevent applying too much rotational force or torque on a tap 210 or pedicle screw 270A-D. A sensor system 20A-20C may also include tissue discriminators that detect the tissue type(s) near a tap 210 or pedicle screw 270A-D where the architecture 10 may be trained to prevent placing or advancing a tap 210 or a pedicle screw 270A-D into or near certain tissue types.

Once an activity is complete (112A of FIG. 3A), activities 106A and 108A may be repeated for other activities of a medical procedure (activity 114A). In an embodiment, activities 106A and 108A may be repeated for placement of other pedicle screws 270A-D by a medical professional 70B in other vertebrae 230A pedicles 232. Once all the activities are complete, a I/M/P 202E may be created for the activity by a User 70B, training system 40A-40C, or machine learning system (50A-50C) (such as I/M/P 202E as described above and shown FIG. 4P). It is noted that I/M/P 202E form a horizontal trajectory 189A, 189B. Another I/M/P may be created via FIG. 4B to form vertical trajectory 234A-F where the two trajectories may be combined to form a 3-D trajectory in an embodiment.

As shown in FIG. 3A, a User 70B, training system 40A-40C, or machine learning system (50A-50C) may then determine the types and number of robotic systems 60A-60C and sensor systems 20A-20C that may be needed to perform a medical procedure activity or steps of an activity (activity 116A) based on one or more develop I/M/P 202E. A medical professional 70B, engineer or other professional may interact with one or more training systems 40A-40C to provide input on the robotic systems 60A-60C and sensor systems 20A-20C to be employed and thus trained to perform a medical procedure activity.

Based on the selected robotic systems 60A-60C and sensor systems 20A-20C to be employed to conduct/perform a particular medical procedure activity, one or more training systems 40A-40C may retrieve related sensor data 80 from training databases 30A-30C to train neural network systems 50A-50C to control the selected robotic systems 60A-60C and sensor systems 20A-20C (activity 118A) based on one or more develop I/M/P 202E. In an embodiment, one or more neural network systems 50A-50C may be trained to control one or more robotic systems 60A-60C and sensor systems 20A-20C. The neural network systems 50A-50C may be used for all relevant sensor data 80A (activity 122A) and for all robotic systems 60A-60C and sensor systems 20A-20C to be employed to conduct/perform a particular medical procedure activity (activity 124A) based on one or more develop I/M/P 202E. Activities 116A to 124A may be repeated for other activities of a medical procedure.

In activity 102A, algorithm 100A first determined whether a medical procedure was new to architecture 10. When a medical procedure or activity is not new, architecture 10 may still perform activities 128A to 146A, which are similar to activities 106A to 126A discussed above to update/improve one or more neural network systems 50A-50C training.

Once neural network systems 50A-50C have been trained, architecture 10 may be employed to perform one or more activities of a medical procedure. FIG. 3B is a flow diagram 100B illustrating several methods for employing neural network systems 50A-50C to control one or more robotic systems 60A-60C and sensor systems 20A-20C to perform activities of a medical procedure according to various embodiments. In an embodiment, a medical professional 70B may direct architecture 10 to perform one or more activities of a medical procedure. Based on the medical professional's 70B selection, architecture 10 may engage or activate and initially position one or more sensor systems 20A-20C based on the selected activity (Activity 102B) and based on one or more develop I/M/P 202E. One or more neural network systems 50A-50C may be trained to control/position/engage sensor systems 20A-20C in addition to one or more robotic systems 60A-60C for a particular medical procedure based on one or more develop I/M/P 202E. One or more training systems 40A-40C may train one or more neural network systems 50A-50C to control the operation of one or more sensor systems 20A-20C during the performance of a medical procedure activity based on one or more develop I/M/P 202E. As noted in embodiment, one or more sensor systems 20A-20C may be part of one or more robotic systems 60A-60C.

Architecture 10 via one or more neural network systems 50A-50C or robotic systems 60A-60C may cause the activated sensor systems 20A-20C to start optimally sampling sensor data (generated, received, and position) 80D that is considered in real time by one or more neural network systems 50A-50C to control one or more robotic systems 60A-60C and sensor systems 20A-20C (activity 104B) based on one or more develop I/M/P 202E. When the initial sensor data 80D is not considered with acceptable parameters by the one or more neural network systems 50A-50C (activity 106B), a medical professional 70B or system user may be notified of the measured parameters (activity 124B). The medical professional 70B or system user may be notified via wired or wireless communication systems and may direct architecture 10 to continue the activity (activity 128B) or halt the operation.

It is noted the sensor systems 20A-20C deployed during an activity may vary during the activity. If the initial sensor data 80D is determined to be within parameters (activity 106B), then one or more robotics systems 60A-60C may be deployed and controlled by one or more neural network systems 50A-50C based on one or more develop I/M/P 202E (activity 108B). One or more neural network systems 50A-50C may control the operation/position of one or more sensor systems 20A-20C, review their sensor data 80D, and continue deployment of one or more robotic systems 60A-60C and sensor systems 20A-20C needed for an activity while the sensor data 80D is within parameters (activities 112B, 114B, 116B) until the activity is complete (activity 118B) and procedure is complete (activity 122B) based on one or more develop I/M/P 202E.

When during the deployment of one or more robotic systems 60A-60C and sensor systems 20A-20C, sensor data 80D is determined by one or more neural network systems 50A-50C to be not within acceptable parameters (activity 114B), architecture 10 may inform a medical professional 70B or system user of the measured parameters (activity 124B). The medical professional 70B or system user may be notified via wired or wireless communication systems and may direct architecture 10 to continue the activity (activity 128B) or halt the operation.

As noted, architecture 10 may also be employed to developing a base logic/model/procedure (L/M/P) and training/improving neural network systems to enable robot(s) to diagnose a medical condition of a patient 70A based on a developed L/M/P. For example, FIG. 3C is a flow diagram 100C illustrating several methods for developing a base logic/model/procedure (L/M/P) and training/improving neural network systems 50A-50C to enable robot(s) 60A-60C to diagnose a medical condition based on a developed L/M/P according to various embodiments. FIG. 3D is a flow diagram 100D illustrating several methods for employing one or more neural network systems 50A-50C to control one or more robot system(s) 60A-60C and sensor systems 20A-20C to diagnose medical condition(s) according to a medical procedure based on a developed L/M/P according to various embodiments.

As shown in FIG. 3C, algorithm 100C is similar to algorithm 100A and includes activities 102C to 134C similar to algorithm's 100A activities 102A-146A. As shown in FIG. 3D, algorithm 100D is similar to algorithm 100B and includes activities 102D to 134D similar to algorithm's 100B activities 102B-128B. Algorithm 100D of FIG. 3D further includes reporting one or more detected medical conditions to a user (activities 124D and 126D). FIG. 3C is directed to learning new medical conditions versus a medical procedure and FIG. 3D is directed to employing architecture 10 to detect or diagnose one or more medical conditions. It is noted, however that the process of detecting or diagnosing one or more medical conditions of a patient 70A may also follow or employ a medical procedure having activities. Accordingly, architecture 10 may be employed to conduct medical procedure activities that are directed to detecting or diagnosing one or more medical conditions as well as treating one or more medical conditions.

FIG. 8 illustrates a block diagram of a device 290 that may be employed in an architecture 10. The device 290 may represent elements of any of the components of architecture 10 including one or more sensor systems 20A-20C, one or more training databases 30A-C, one or more training systems 40A-40C, one or more neural network systems 50A-50C, and one or more robotic systems 60A-60C. The device 290 may include a central processing unit (CPU) 292, a graphics processing unit (GPU) 291, a random access memory (RAM) 294, a read only memory (ROM) 297, a local wireless/GPS modem/transceiver 314, a touch screen display 317, an input device (keyboard or others) 325, a camera 327, a speaker 315, a rechargeable electrical storage element 326, an electric motor 332, and an antenna 316. The CPU 292 may include neural network modules 324 in an embodiment. In an embodiment, a device 290 may include multiple CPU where a CPU may be application specific integrated circuits (ASIC) dedicated to particular functions including a graphical processing unit and digital signal processor. The RAM 294 may include a queue or table 318 where the queue 318 may be used to store session events and sensor data 80A-D. The RAM 294 may also include program data, algorithm, and session data and session instructions. The rechargeable electrical storage element 326 may be a battery or capacitor in an embodiment.

The modem/transceiver 314 or CPU 292 may couple, in a well-known manner, the device 290 in architecture 10 to enable communication with devices 20A-60C. The modem/transceiver 314 may also be able to receive global positioning signals (GPS) and the CPU 292 may be able to convert the GPS signals to location data that may be stored in the RAM 314. The ROM 297 may store program instructions to be executed by the CPU 292 or neural network module 324. The electric motor 332 may control to the position of a mechanical structure in an embodiment.

The modules may include hardware circuitry, single or multi-processor circuits, memory circuits, software program modules and objects, firmware, and combinations thereof, as desired by the architect of the architecture 10 and as appropriate for particular implementations of various embodiments. The apparatus and systems of various embodiments may be useful in applications other than a sales architecture configuration. They are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, single or multi-processor modules, single or multiple embedded processors, data switches, and application-specific modules, including multilayer, multi-chip modules. Such apparatus and systems may further be included as sub-components within and couplable to a variety of electronic systems, such as televisions, cellular telephones, personal computers (e.g., laptop computers, desktop computers, handheld computers, tablet computers, etc.), workstations, radios, video players, audio players (e.g., mp3 players), vehicles, medical devices (e.g., heart monitor, blood pressure monitor, etc.) and others. Some embodiments may include a number of methods.

It may be possible to execute the activities described herein in an order other than the order described. Various activities described with respect to the methods identified herein can be executed in repetitive, serial, or parallel fashion. A software program may be launched from a computer-readable medium in a computer-based system to execute functions defined in the software program. Various programming languages may be employed to create software programs designed to implement and perform the methods disclosed herein. The programs may be structured in an object-orientated format using an object-oriented language such as Java or C++. Alternatively, the programs may be structured in a procedure-orientated format using a procedural language, such as assembly, C, python, or others. The software components may communicate using a number of mechanisms well known to those skilled in the art, such as application program interfaces or inter-process communication techniques, including remote procedure calls. The teachings of various embodiments are not limited to any particular programming language or environment.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus, the following claims are hereby incorporated into the Detailed Description, with each claim standing on its own as a separate embodiment.

What is claimed is:

1. A method of forming an automated system to perform an activity of a medical procedure for a patient, including:
    initializing positioning a sensor system to monitor an aspect of the medical procedure activity;
    starting the medical procedure activity;
    sampling sensor system data until the medical procedure activity to be automated is complete;
    forming a base model of an activity of a medical procedure for a patient based on sampled sensor system data for a region of the patient to be affected by the activity;
    determining one of a target or access to target for a region to be affected by the activity based on the formed base model;
    determining the number of robotic systems needed to perform the medical procedure activity based on the base model and one of the target or access to target; and
    training an automated robotic control system to control one of the determined robotic systems to perform the medical procedure activity based on the sampled sensor system data, the formed base model, and one of the target or access to target.

2. The method of forming an automated system to perform an activity of a medical procedure for a patient of claim 1, including initializing positioning a plurality of sensor systems to monitor a plurality of aspects of the medical procedure activity.

3. The method of forming an automated system to perform an activity of a medical procedure for a patient of claim 1, wherein the sensor system data includes the sensor system physical location relative to the patient and one or received data and processed received data.

4. The method of forming an automated system to perform an activity of a medical procedure for a patient of claim 1, wherein the sensor system data includes the sensor system physical location relative to the patient and one of sensor system received data and processed received data.

5. The method of forming an automated system to perform an activity of a medical procedure for a patient of claim 1, wherein the sensor system data includes the sensor system physical location relative to the patient, generated sensor system data, and one of received data and processed received data.

6. The method of forming an automated system to perform an activity of a medical procedure for a patient of claim 2, storing sampling sensor system data from the plurality of sensor systems in a training database.

7. The method of forming an automated system to perform an activity of a medical procedure for a patient of claim 6, employing a training system to train an automated robotic control system to control one of the determined robotic systems to perform the medical procedure activity based on the sampled sensor system data from the plurality of sensor systems stored in the training database, the formed base model, and one of the target or access to target.

8. The method of forming an automated system to perform an activity of a medical procedure for a patient of claim 1, wherein the automated robotic control system includes neural networks.

9. The method of forming an automated system to perform an activity of a medical procedure for a patient of claim 1, employing a training system to train an automated robotic control system including neural networks to control one of the determined robotic systems to perform the medical procedure activity based on the sampled sensor system data, the formed base model, and one of the target or access to target.

10. The method of forming an automated system to perform an activity of a medical procedure for a patient of claim 6, employing a training system to train an automated robotic control system including neural networks to control one of the determined robotic systems to perform the medical procedure activity based on the sampled sensor system data from the plurality of sensor systems stored in the training database, the formed base model, and one of the target or access to target.

11. A system for forming an automated system to perform an activity of a medical procedure for a patient, including:
    a sensor system positioned to monitor an aspect of the medical procedure activity;
    a base model formation system to form a base model for a region of the patient to be affected by the activity of a medical procedure based on monitored sensor system data, the base model including one or landmarks and one of a target or access to target;
    an automated robotic control system to control a robotic system to perform an aspect of the medical procedure activity based on monitored sensor system data and the formed base model;
    a training system that trains an automated robotic control system to control a robotic system to perform an aspect of the medical procedure activity based on monitored sensor system data and the formed base model.

12. The system for forming an automated system to perform an activity of a medical procedure for a patient of claim 11, including a plurality of sensor systems positioned to monitor a plurality of aspects of the medical procedure activity.

13. The system for forming an automated system to perform an activity of a medical procedure for a patient of claim 11, wherein the sensor system data includes the sensor system physical location relative to the patient and one or received data and processed received data.

14. The system for forming an automated system to perform an activity of a medical procedure for a patient of claim 11, wherein the sensor system data includes the sensor system physical location relative to the patient and one of sensor system received data and processed received data.

15. The system for forming an automated system to perform an activity of a medical procedure for a patient of claim 11, wherein the sensor system data includes the sensor system physical location relative to the patient, generated sensor system data, and one of received data and processed received data.

16. The system for forming an automated system to perform an activity of a medical procedure for a patient of claim 12, further including a training database system for storing monitored sensor system data from the plurality of sensor systems.

17. The system for forming an automated system to perform an activity of a medical procedure for a patient of claim 16, further including a training system to train an automated robotic control system to a robotic system to perform the medical procedure activity based on the monitored sensor system data from the plurality of sensor systems stored by the training database system and the formed base model.

18. The system for forming an automated system to perform an activity of a medical procedure for a patient of claim 11, wherein the automated robotic control system includes neural networks.

19. The system for forming an automated system to perform an activity of a medical procedure for a patient of claim 11, further including a training system to train an automated robotic control system including neural networks to control a robotic system to perform the medical procedure activity based on the sampled sensor system data and the formed base model.

20. The system for forming an automated system to perform an activity of a medical procedure for a patient of claim 16, including a training system to train an automated robotic control system including neural networks to control one of a robotic system to perform the medical procedure activity based on the sampled sensor system data from the plurality of sensor systems stored in the training database and the formed base model.

* * * * *